United States Patent
Kato

(10) Patent No.: US 11,516,420 B2
(45) Date of Patent: Nov. 29, 2022

(54) IMAGING SYSTEM AND ENDOSCOPE SYSTEM

(71) Applicant: OLYMPUS CORPORATION, Hachioji (JP)

(72) Inventor: Hideki Kato, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/038,291

(22) Filed: Sep. 30, 2020

(65) Prior Publication Data

US 2021/0014448 A1 Jan. 14, 2021

Related U.S. Application Data

(63) Continuation of application No. PCT/JP2019/009975, filed on Mar. 12, 2019.

(30) Foreign Application Priority Data

Apr. 4, 2018 (JP) .................... PCT/JP2018/014385

(51) Int. Cl.
*H04N 5/376* (2011.01)
*A61B 1/045* (2006.01)
(Continued)

(52) U.S. Cl.
CPC ........... *H04N 5/3765* (2013.01); *A61B 1/045* (2013.01); *A61B 1/05* (2013.01); *A61B 1/00009* (2013.01); *H04N 5/225* (2013.01); *H04N 7/18* (2013.01)

(58) Field of Classification Search
CPC .......... H04N 5/3765; A61B 1/045; A61B 1/05
(Continued)

(56) References Cited

U.S. PATENT DOCUMENTS

2007/0159526 A1* 7/2007 Abe .................. H04N 5/23203
  348/65
2009/0160973 A1* 6/2009 Hou ........................ G06F 3/14
  348/231.2
(Continued)

FOREIGN PATENT DOCUMENTS

CN         101997629 A  *  3/2011  ........... H03L 7/0807
EP         2 654 285 A1    10/2013
(Continued)

OTHER PUBLICATIONS

International Search Report dated Jun. 4, 2019, issued in counterpart International Application No. PCT/JP2019/009975 with English translation (2 pages).

*Primary Examiner* — Christopher S Kelley
*Assistant Examiner* — Asmamaw G Tarko
(74) *Attorney, Agent, or Firm* — WHDA, LLP

(57) ABSTRACT

An imaging system includes a camera unit and a main body. A clock detection circuit is configured to detect a first clock signal of the camera unit from first digital data transmitted from the camera unit. A phase comparator is configured to generate second digital data that represent a difference between a phase of the first clock signal and a phase of a second clock signal of the main body. A second communicator is configured to perform communication in a second direction in which the second digital data are transmitted to the camera unit in a blanking period. A first clock generation circuit is configured to generate the first clock signal synchronized with the second clock signal on the basis of the second digital data.

14 Claims, 8 Drawing Sheets

(51) Int. Cl.
   *A61B 1/05*   (2006.01)
   *H04N 5/225*  (2006.01)
   *H04N 7/18*   (2006.01)
   *A61B 1/00*   (2006.01)

(58) Field of Classification Search
   USPC .......................................................... 348/65
   See application file for complete search history.

(56) References Cited

U.S. PATENT DOCUMENTS

| | | | |
|---|---|---|---|
| 2009/0213212 A1* | 8/2009 | Nakamura | A61B 1/00006 |
| | | | 348/65 |
| 2012/0320176 A1* | 12/2012 | Tanaka | A61B 1/00016 |
| | | | 348/65 |
| 2013/0235173 A1* | 9/2013 | Segawa | A61B 1/00018 |
| | | | 348/65 |
| 2020/0214540 A1* | 7/2020 | Tanaka | A61B 1/00009 |

FOREIGN PATENT DOCUMENTS

| | | | | |
|---|---|---|---|---|
| JP | 5-336425 A | 12/1993 | | |
| JP | 2000-134633 A | 5/2000 | | |
| JP | 2009-22579 A | 2/2009 | | |
| JP | 2012-49919 A | 3/2012 | | |
| JP | 2013-165369 A | 8/2013 | | |
| JP | 2013-165772 A | 8/2013 | | |
| JP | 2013165772 A * | 8/2013 | ............... | A61B 1/04 |
| JP | 2016-106902 A | 6/2016 | | |
| WO | 2013/031514 A1 | 3/2013 | | |
| WO | WO-2013031514 A1 * | 3/2013 | ......... | A61B 1/00018 |

* cited by examiner

IMAGING SYSTEM AND ENDOSCOPE SYSTEM

The present application claims priority to PCT Patent Application No. PCT/JP2018/014385, filed on Apr. 4, 2018 and is a continuation application based on PCT Patent Application No. PCT/JP2019/009975, filed on Mar. 12, 2019, and the content of the PCT patent applications is incorporated herein by reference.

BACKGROUND OF THE INVENTION

Field of the Invention

The present invention relates to an imaging system and an endoscope system.

Description of Related Art

An imaging system that transmits an imaging signal by using a long cable has been developed. The imaging system includes a camera unit and a main body. In the imaging system, it is necessary to supply a clock signal to an imaging device that generates the imaging signal.

In a system disclosed in Japanese Unexamined Patent Application, First Publication No. HS-336425, a camera head and a main body (camera control unit) are connected together by two signal lines. The camera head corresponds to the camera unit. An image signal with which a clock signal of the camera head has been mixed is transmitted from the camera head to the main body. In the main body, the image signal and the clock signal are separated from each other. The clock signal of the camera head and a clock signal of the main body are compared with each other by a phase comparator. The difference between the two clock signals is transmitted to the camera head as a phase error signal. The phase error signal is a DC signal (direct current signal). The camera head performs feedback control on a PLL circuit by using the phase error signal and thus causes the clock signal of the camera head to be synchronized with the clock signal of the main body.

In an electronic endoscope device disclosed in Japanese Unexamined Patent Application. First Publication No. 2016-106902, a clock signal of a video scope is supplied from a processor. The video scope corresponds to the camera unit and the processor corresponds to the main body. A synchronization detection code is transmitted from the video scope to the processor in a blanking period. In the processor, processing for synchronization is executed on the basis of the synchronization detection code.

SUMMARY OF THE INVENTION

According to a first aspect of the present invention, an imaging system includes a camera unit and a main body. The camera unit includes a solid-state imaging device, a first clock generation circuit, a signal generation circuit, a data generation circuit, and a first communicator. The solid-state imaging device is configured to generate image data on the basis of a control signal. The first clock generation circuit is configured to generate a first clock signal. The signal generation circuit is configured to generate the control signal on the basis of the first clock signal. The data generation circuit is configured to generate first digital data by embedding the first clock signal into the image data. The first communicator is configured to perform communication in a first direction in which the first digital data are transmitted to the main body in a period different from a blanking period. The main body includes a second communicator, a clock detection circuit, a second clock generation circuit, and a phase comparator. The second communicator is configured to receive the first digital data transmitted from the camera unit. The clock detection circuit is configured to detect the first clock signal from the first digital data. The second clock generation circuit is configured to generate a second clock signal. The phase comparator is configured to compare a phase of the first clock signal with a phase of the second clock signal and generate second digital data that represent a difference between the phase of the first clock signal and the phase of the second clock signal. The second communicator is configured to perform communication in a second direction in which the second digital data are transmitted to the camera unit in the blanking period. The first communicator is configured to receive the second digital data transmitted from the main body in the blanking period. The camera unit and the main body are connected by a signal line through which the first digital data pass in the communication in the first direction and the second digital data pass in the communication in the second direction. The first clock generation circuit is configured to generate the first clock signal synchronized with the second clock signal on the basis of the second digital data.

According to a second aspect of the present invention, in the first aspect, the data generation circuit may be configured to generate an end code that represents a timing at which generation of the image data is intermittently stopped. The first communicator may be configured to transmit the end code to the main body when the generation of the image data is intermittently stopped. The second communicator may be configured to receive the end code transmitted from the camera unit. The second communicator may be configured to start transmission of the second digital data when the end code is received.

According to a third aspect of the present invention, in the second aspect, the main body may further include a code generation circuit configured to generate a start code that represents a timing at which the generation of the image data is started. The second communicator may be configured to transmit the start code to the camera unit in the blanking period. The first communicator may be configured to receive the start code transmitted from the main body in the blanking period. The signal generation circuit may be configured to generate the control signal for causing the solid-state imaging device to start the generation of the image data when the start code is received. The data generation circuit may be configured to start generation of the first digital data when the start code is received. The first communicator may be configured to start transmission of the first digital data when the start code is received.

According to a fourth aspect of the present invention, in any one of the first to third aspects, the camera unit may further include a memory configured to hold the second digital data. The first clock generation circuit may be configured to generate the first clock signal on the basis of the second digital data held in the memory.

According to a fifth aspect of the present invention, in the first aspect, the main body may further include a frequency comparator configured to compare a frequency of the first clock signal with a frequency of the second clock signal and generate third digital data that represent a difference between the frequency of the first clock signal and the frequency of the second clock signal. The second communicator may be configured to transmit the third digital data to the camera unit in the blanking period. The first communicator may be configured to receive the third digital data transmitted from the main body in the blanking period. The first clock generation circuit may be configured to generate the first clock signal having the same frequency as the frequency of the second clock signal by adjusting the frequency of the first clock signal on the basis of the third digital data.

According to a sixth aspect of the present invention, in the fifth aspect, the second communicator may be configured to transmit the third digital data to the camera unit until the frequency comparator detects that the frequency of the first clock signal and the frequency of the second clock signal are the same. The second communicator may be configured to transmit the second digital data to the camera unit after the frequency comparator detects that the frequency of the first clock signal and the frequency of the second clock signal are the same.

According to a seventh aspect of the present invention, in the fifth aspect, the blanking period may include a first blanking period and a second blanking period after the first blanking period. The second communicator may be configured to transmit the third digital data to the camera unit in the first blanking period. The second communicator may be configured to transmit the second digital data to the camera unit in the second blanking period.

According to an eighth aspect of the present invention, in the fifth aspect, the second communicator may be configured to transmit a start code that represents a timing at which the generation of the image data is started to the camera unit in the blanking period. The first communicator may be configured to receive the start code transmitted from the main body in the blanking period. The signal generation circuit may be configured to generate the control signal for causing the solid-state imaging device to start the generation of the image data when the start code is received. The data generation circuit may be configured to start generation of the first digital data when the start code is received. The first communicator may be configured to start transmission of the first digital data when the start code is received. The first communicator may be configured to transmit an end code that represents a timing at which generation of data of one row included in the image data is completed to the main body when the solid-state imaging device completes the generation of the data of the one row. The second communicator may be configured to receive the end code transmitted from the camera unit. The frequency comparator may be configured to generate a count value by counting a pulse of the second clock signal in a counting period included in a horizontal reading period from a timing at which the start code is transmitted to a timing at which the end code is received. The frequency comparator may be configured to generate the third digital data on the basis of a result of comparing the count value with an estimation value calculated in advance. The estimation value is a count value that is assumed to be obtained by counting the pulse of the second clock signal in the counting period when it is assumed that the frequency of the first clock signal and the frequency of the second clock signal are the same.

According to a ninth aspect of the present invention, in the fifth aspect, the first clock generation circuit may include a ring oscillator circuit including at least four delay circuits. The frequency comparator may be configured to generate the third digital data including first frequency adjustment data and second frequency adjustment data. The first clock generation circuit may be configured to adjust the frequency of the first clock signal by adjusting a number of the delay circuits that are annularly connected together on the basis of the first frequency adjustment data and by adjusting an amount of current supplied to the delay circuits on the basis of the second frequency adjustment data.

According to a tenth aspect of the present invention, in the ninth aspect, the frequency comparator may be configured to generate the third digital data that include the first frequency adjustment data as an upper bit and include the second frequency adjustment data as a lower bit.

According to an eleventh aspect of the present invention, in any one of the fifth to tenth aspects, the signal generation circuit may include a digital-analog converter and a voltage-controlled oscillator. The digital-analog converter is configured to convert the third digital data into an analog voltage. The voltage-controlled oscillator is configured to generate the first clock signal on the basis of the analog voltage.

According to a twelfth aspect of the present invention, an imaging system includes a camera unit and a main body. The camera unit includes a solid-state imaging device, a first clock generation circuit, a signal generation circuit, a first communicator, and a phase comparator. The solid-state imaging device is configured to generate image data on the basis of a control signal. The first clock generation circuit is configured to generate a first clock signal. The signal generation circuit is configured to generate the control signal on the basis of the first clock signal. The first communicator is configured to transmit the image data to the main body in a period different from a blanking period. The phase comparator is configured to compare a phase of the first clock signal with a phase of a second clock signal and generate digital phase data that represent a difference between the phase of the first clock signal and the phase of the second clock signal. The main body includes a second communicator and a second clock generation circuit. The second communicator is configured to receive the image data transmitted from the camera unit. The second clock generation circuit is configured to generate the second clock signal. The second communicator is configured to transmit the second clock signal to the camera unit in the blanking period. The first communicator is configured to receive the second clock signal transmitted from the main body in the blanking period. The first communicator is configured to transmit the digital phase data to the main body in the blanking period. The second communicator is configured to receive the digital phase data transmitted from the camera unit in the blanking period. The second clock generation circuit is configured to generate the second clock signal synchronized with the first clock signal on the basis of the digital phase data.

According to a thirteenth aspect of the present invention, in the twelfth aspect, the camera unit may further include a frequency comparator configured to compare a frequency of the first clock signal with a frequency of the second clock signal and generate digital frequency data that represent a difference between the frequency of the first clock signal and the frequency of the second clock signal. The first communicator may be configured to transmit the digital frequency data to the main body in the blanking period. The second communicator may be configured to receive the digital frequency data transmitted from the camera unit in the blanking period. The second clock generation circuit may be configured to generate the second clock signal having the same frequency as the frequency of the first clock signal by adjusting the frequency of the second clock signal on the basis of the digital frequency data.

According to a fourteenth aspect of the present invention, in any one of the first to thirteenth aspects, an endoscope system includes a scope and the imaging system. The scope includes a tip end and a base end. The solid-state imaging device is disposed in the tip end. The main body is connected to the base end.

DETAILED DESCRIPTION OF THE INVENTION

Hereinafter, embodiments of the present invention will be described with reference to the drawings. Each of the embodiments will be described in detail by using an electronic endoscope system as an example of an imaging system.

First Embodiment

Figure 1:
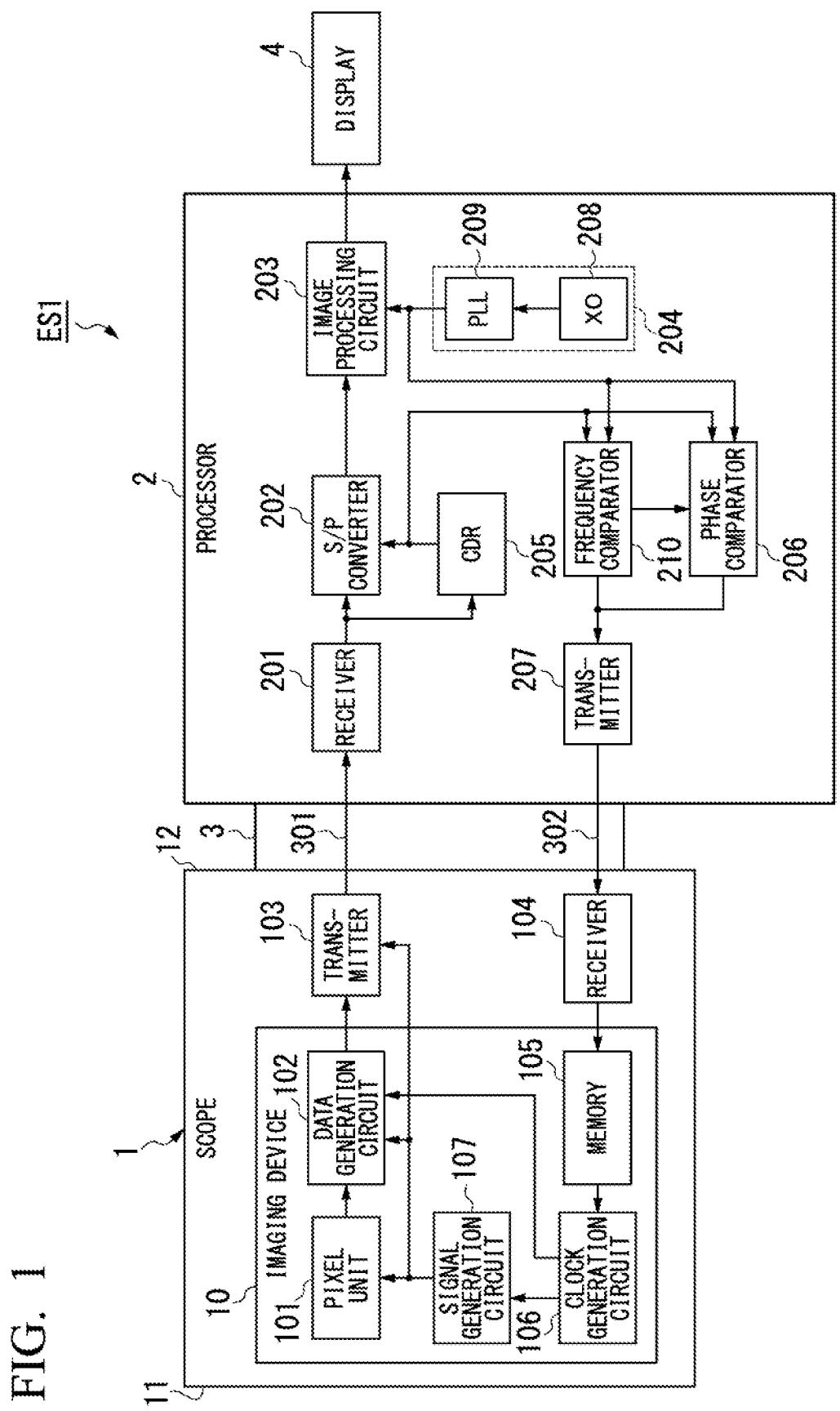
FIG. 1 is a block diagram showing a configuration of an electronic endoscope system according to a first embodiment of the present invention.

FIG. 1 shows a configuration of an electronic endoscope system ES1 according to a first embodiment of the present invention. The electronic endoscope system ES1 shown in FIG. 1 includes a scope 1, a processor 2, a cable 3, and a display 4.

The scope 1 is a camera unit. The scope 1 includes an imaging device 10, a transmitter 103, and a receiver 104. The imaging device 10 includes a pixel unit 101, a data generation circuit 102, a memory 105, a clock generation circuit 106, and a signal generation circuit 107. The processor 2 is a main body. The processor 2 includes a receiver 201, an S/P converter 202, an image processing circuit 203, a clock generation circuit 204, a clock data recovery circuit 205, a phase comparator 206, a transmitter 207, and a frequency comparator 210. Hereinafter, the clock data recovery circuit 205 is called a CDR circuit 205.

A schematic configuration of the electronic endoscope system ES1 will be described. The imaging device 10 is a solid-state imaging device. The imaging device generates image data on the basis of a control signal. The clock generation circuit 106 (first clock generation circuit) generates a first clock signal. The signal generation circuit 107 generates the control signal on the basis of the first clock signal. The data generation circuit 102 generates first digital data by embedding the first clock signal into the image data.

The transmitter 103 (first transmitter) transmits the first digital data to the processor 2. In this way, the transmitter 103 performs communication in a first direction. The first direction is a direction from the scope 1 toward the processor 2. The receiver 201 (second receiver) receives the first digital data transmitted from the scope 1. The CDR circuit 205 (clock detection circuit) detects the first clock signal from the first digital data. The clock generation circuit 204 (second clock generation circuit) generates a second clock signal. The phase comparator 206 compares the phase of the first clock signal with the phase of the second clock signal and generates second digital data that represent the difference between the phase of the first clock signal and the phase of the second clock signal. The transmitter 207 (second transmitter) transmits the second digital data to the scope 1. In this way, the transmitter 207 performs communication in a second direction. The second direction is a direction from the processor 2 toward the scope 1. The receiver 104 (first receiver) receives the second digital data transmitted from the processor 2. The scope 1 and the processor 2 are connected by the cable 3 through which the first digital data pass in the communication in the first direction and the second digital data pass in the communication in the second direction. The clock generation circuit 106 generates the first clock signal synchronized with the second clock signal on the basis of the second digital data.

The frequency comparator 210 compares the frequency of the first clock signal with the frequency of the second clock signal and generates third digital data that represent the difference between the frequency of the first clock signal and the frequency of the second clock signal. The transmitter 207 transmits the third digital data to the scope 1. The receiver 104 receives the third digital data transmitted from the processor 2. The clock generation circuit 106 generates the first clock signal having the same frequency as the frequency of the second clock signal by adjusting the frequency of the first clock signal on the basis of the third digital data.

For example, the transmitter 207 transmits the third digital data to the scope 1 before transmitting the second digital data. After the frequency comparator 210 detects that the frequency of the first clock signal and the frequency of the second clock signal are the same, the transmitter 207 transmits the second digital data to the scope 1.

The scope 1 includes a tip end 11 and a base end 12. The imaging device 10 is disposed at the tip end 11. The processor 2 is connected to the base end 12.

A detailed configuration of the electronic endoscope system ES1 will be described. The cable 3 electrically connects the scope 1 and the processor 2 together. The processor 2 is connected to the base end 12 of the scope 1 via the cable 3. The cable 3 includes a signal line 301 and a signal line 302. The transmitter 103 and the receiver 201 are connected to the signal line 301. The receiver 104 and the transmitter 207 are connected to the signal line 302.

The receiver 104 receives the second digital data and the third digital data transmitted by the transmitter 207. The memory 105 holds the second digital data and the third digital data received by the receiver 104. The memory 105 outputs the second digital data and the third digital data to the clock generation circuit 106.

The clock generation circuit 106 generates the first clock signal on the basis of the second digital data and the third digital data held in the memory 105. The first clock signal is synchronized with the second clock signal of the processor 2. The phase of the first clock signal is controlled by using the second digital data. The frequency of the first clock signal is controlled by using the third digital data. The first clock signal generated by the clock generation circuit 106 is output to the signal generation circuit 107 and the data generation circuit 102.

For example, the third digital data are received before the second digital data are received. When the third digital data are received, the clock generation circuit 106 adjusts the frequency of the first clock signal on the basis of the third digital data. When the second digital data are received, the clock generation circuit 106 adjusts the phase of the first clock signal on the basis of the second digital data. Therefore, after adjusting the frequency of the first clock signal on the basis of the third digital data, the clock generation circuit 106 adjusts the phase of the first clock signal on the basis of the second digital data.

The signal generation circuit 107 generates the control signal for controlling timings of operations of the pixel unit 101, the data generation circuit 102, and the transmitter 103. The control signal generated by the signal generation circuit 107 is output to the pixel unit 101, the data generation circuit 102, and the transmitter 103.

The pixel unit 101 generates a pixel signal at a timing that is based on the control signal output from the signal generation circuit 107. The pixel signal output from the pixel unit 101 is converted into the image data. The data generation circuit 102 generates the first digital data at a timing that is based on the control signal output from the signal generation circuit 107. The image data are serial data including multiple pieces of pixel data. For example, the data generation circuit 102 generates the first digital data by inserting data of the first clock signal between the multiple pieces of pixel data. A method of generating the first digital data is not limited to this method. The first digital data generated by the data generation circuit 102 are output to the transmitter 103. The transmitter 103 transmits the first digital data to the processor 2.

The first digital data transmitted from the transmitter 103 pass through the signal line 301. The receiver 201 receives the first digital data transmitted by the transmitter 103. The first digital data received by the receiver 201 are output to the S/P converter 202 and the CDR circuit 205. The CDR circuit 205 reproduces the first clock signal from the first digital data. Reproduction of a clock signal is executed on the basis of a general clock-data-recovery technology. The first clock signal reproduced by the CDR circuit 205 is output to the receiver 201, the S/P converter 202, the phase comparator 206, and the frequency comparator 210. The receiver 201 receives the first digital data on the basis of the first clock signal. The S/P converter 202 converts the image data that are serial data into parallel data on the basis of the first clock signal. The image data are converted into the parallel data and are output to the image processing circuit 203.

The clock generation circuit 204 includes a crystal oscillator 208 and a phase locked loop (PLL) circuit 209. Hereinafter, the crystal oscillator 208 is called an XO 208. The XO 208 includes a quartz crystal oscillator. The XO 208 and the PLL circuit 209 generate the second clock signal. The second clock signal generated by the XO 208 and the PLL circuit 209 is output to the image processing circuit 203, the phase comparator 206, and the frequency comparator 210.

The image processing circuit 203 performs signal processing on the image data on the basis of the second clock signal. For example, the signal processing performed by the image processing circuit 203 is noise reduction, gamma correction, demosaicing processing, and the like. The image data are output from the image processing circuit 203 to the display 4. The display 4 displays an image on the basis of the image data.

The frequency comparator 210 compares the frequency of the first clock signal with the frequency of the second clock signal. For example, the frequency comparator 210 includes a counter circuit and counts a pulse of the first clock signal and a pulse of the second clock signal in a predetermined period. Counting a pulse means counting the number of pulses. The count value (pulse number) of the first clock signal represents the frequency of the first clock signal. The count value (pulse number) of the second clock signal represents the frequency of the second clock signal. For example, the predetermined period corresponds to a horizontal reading period. In the horizontal reading period, the pixel signal is read from the pixel 111 of one row and data of one row included in the image data are output from the imaging device 10.

While the data of one row included in the image data are received by the receiver 201, the frequency comparator 210 counts a pulse of each of the first clock signal and the second clock signal. The frequency comparator 210 calculates the difference between the count value of the first clock signal and the count value of the second clock signal. The frequency comparator 210 generates the third digital data that represent the calculated difference. The third digital data generated by the frequency comparator 210 are output to the transmitter 207. The transmitter 207 transmits the third digital data to the scope 1. The third digital data transmitted from the transmitter 207 pass through the signal line 302.

When the count value of the first clock signal and the count value of the second clock signal match each other, the frequency comparator 210 detects that the frequency of the first clock signal and the frequency of the second clock signal match each other. At this time, the frequency comparator 210 outputs a notification signal to the phase comparator 206. The notification signal represents that the first clock signal having the same frequency as the frequency of the second clock signal has been generated.

After the notification signal is output from the frequency comparator 210, the phase comparator 206 compares the phase of the first clock signal with the phase of the second clock signal. The phase comparator 206 generates the second digital data that represent the difference between the phase of the first clock signal and the phase of the second clock signal. The second digital data generated by the phase comparator 206 are output to the transmitter 207. The transmitter 207 transmits the second digital data to the scope 1. The second digital data transmitted from the transmitter 207 pass through the signal line 302.

For example, a pixel signal is generated in a plurality of pixels disposed in an N-th row of the pixel unit 101 and the pixel signal is output from the pixel unit 101. The numeral N is a natural number. Data of the N-th row included in the image data are generated on the basis of the pixel signal read from the plurality of pixels disposed in the N-th row. The data generation circuit 102 generates the first digital data including the data of the N-throw. The transmitter 103 transmits the first digital data including the data of the N-th row to the processor 2. While the first digital data including the data of the N-th row are received by the receiver 201, the frequency comparator 210 counts a pulse of each of the first clock signal and the second clock signal and generates the third digital data. After reception of the first digital data including the data of the N-th row is completed, the transmitter 207 transmits the third digital data to the scope 1.

After the pixel signal is read from the plurality of pixels disposed in the N-th row, a pixel signal is generated in a plurality of pixels disposed in an (N+1)-th row of the pixel unit 101 and the pixel signal is output from the pixel unit 101. Data of the (N+1)-th row included in the image data are generated on the basis of the pixel signal read from the plurality of pixels disposed in the (N+1)-th row. The data generation circuit 102 generates the first digital data including the data of the (N+1)-th row. The transmitter 103 transmits the first digital data including the data of the (N+1)-th row to the processor 2. While the first digital data including the data of the (N+1)-th row are received by the receiver 201, the frequency comparator 210 counts a pulse of each of the first clock signal and the second clock signal.

When the count value of the first clock signal and the count value of the second clock signal are not the same, the frequency comparator 210 generates the third digital data. After reception of the first digital data including the data of the (N+1)-th row is completed, the transmitter 207 transmits the third digital data to the scope 1. The above-described operation is repeated until the count value of the first clock signal and the count value of the second clock signal match each other.

While the first digital data including the data of the (N+k)-th row are received by the receiver 201, the frequency comparator 210 counts a pulse of each of the first clock signal and the second clock signal. The numeral k is a natural number. When the frequency of the first clock signal and the frequency of the second clock signal match each other, the frequency comparator 210 outputs a notification signal to the phase comparator 206.

While the first digital data including the data of the (N+k+1)-th row are received by the receiver 201, the phase comparator 206 compares the phase of the first clock signal with the phase of the second clock signal and generates the second digital data. After reception of the first digital data including the data of the (N+k+1)-th row is completed, the transmitter 207 transmits the second digital data to the scope 1.

The transmitter 103 and the receiver 201 may perform optical communication. For example, the transmitter 103 includes a laser light source and the receiver 201 includes a light receiver. An optical fiber is used as the signal line 301. Similarly, the transmitter 207 and the receiver 104 may perform optical communication. For example, the transmitter 207 includes a laser light source and the receiver 104 includes a light receiver. An optical fiber is used as the signal line 302.

The transmitter 103 and the receiver 201 may perform wireless communication. For example, the transmitter 103 and the receiver 201 include an antenna and a wireless circuit. Similarly, the transmitter 207 and the receiver 104 may perform wireless communication. For example, the transmitter 207 and the receiver 104 include an antenna and a wireless circuit.

At least one of the data generation circuit 102, the memory 105, the clock generation circuit 106, and the signal generation circuit 107 may be disposed outside the imaging device 10. At least one of the transmitter 103 and the receiver 104 may be disposed inside the imaging device 10.

Figure 2:
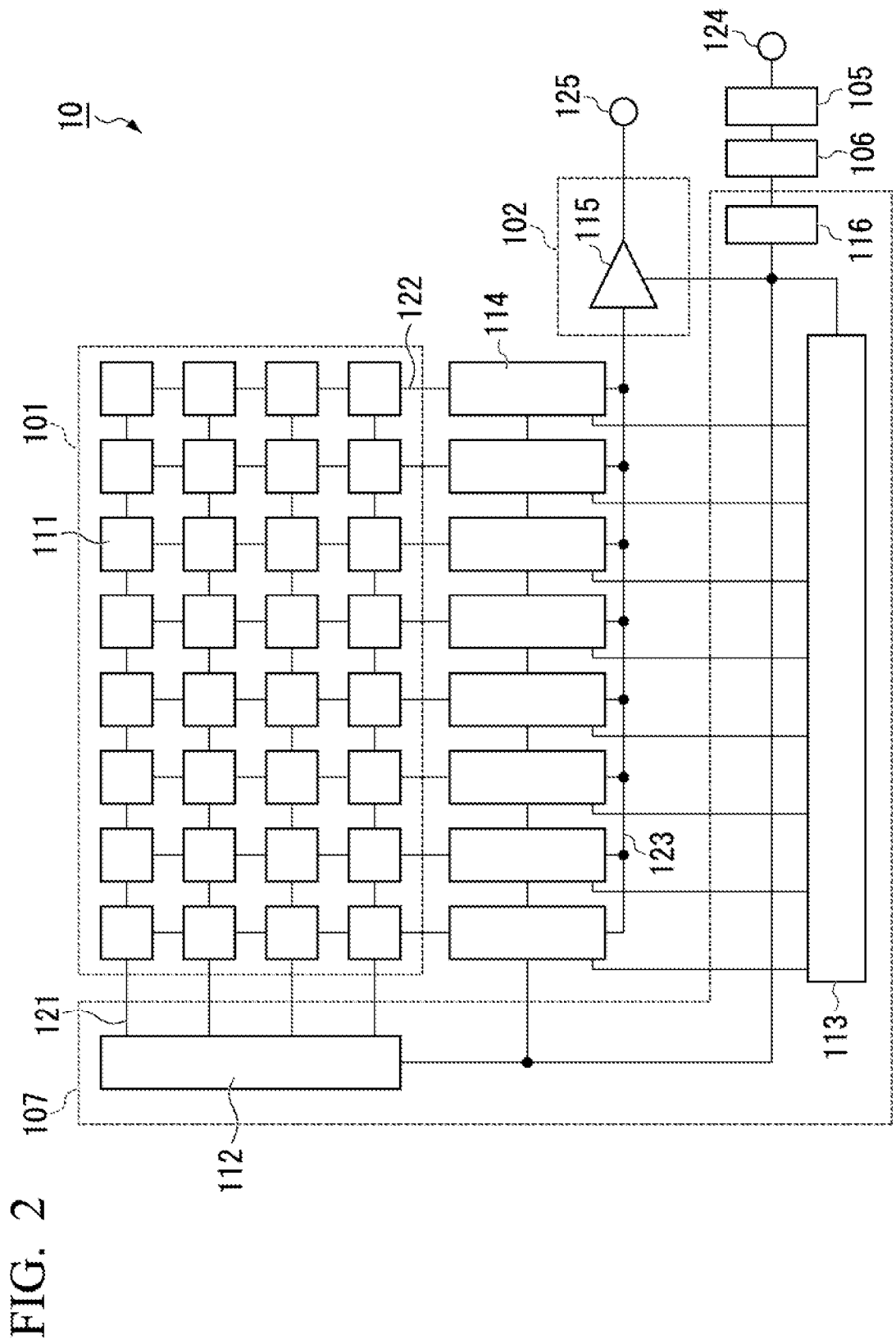
FIG. 2 is a block diagram showing a configuration of an imaging device according to the first embodiment of the present invention.

FIG. 2 shows a configuration of the imaging device 10. An example in which the imaging device 10 is constituted by a CMOS image sensor will be described. The imaging device 10 shown in FIG. 2 includes the pixel unit 101, the data generation circuit 102, the memory 105, the clock generation circuit 106, the signal generation circuit 107, and a column circuit 114.

The memory 105 is connected to a signal input terminal 124. The signal input terminal 124 is connected to the receiver 104. The second digital data and the third digital data received by the receiver 104 are input to the memory 105 via the signal input terminal 124. The second digital data and the third digital data are stored on the memory 105.

The pixel unit 101 includes a plurality of pixels 111 that are two-dimensionally disposed. Each of the plurality of pixels 111 includes a photoelectric conversion element and generates a pixel signal. The number of rows and columns in an array of the plurality of pixels 111 is two or more.

The signal generation circuit 107 includes a vertical scanning circuit 112, a horizontal scanning circuit 113, and a timing generation circuit 116. The timing generation circuit 116 generates a timing signal on the basis of the first clock signal generated by the clock generation circuit 106. For example, the timing signal includes a horizontal synchronizing signal and a vertical synchronizing signal. The timing signal generated by the timing generation circuit 116 is output to the vertical scanning circuit 112, the horizontal scanning circuit 113, and the data generation circuit 102.

The vertical scanning circuit 112 and the horizontal scanning circuit 113 generate a control signal on the basis of the timing signal output from the timing generation circuit 116. A pixel signal is read from the plurality of pixels 111 at a timing that is based on the control signal. The vertical scanning circuit 112 controls the timing at which the pixel signal is read from the plurality of pixels 111 for each row in the array of the plurality of pixels 111. The vertical scanning circuit 112 outputs the control signal to a row control line 121 connected to the pixels 111 of each row. In this way, the vertical scanning circuit 112 controls the output of the control signal from the pixels 111 of each row to a vertical signal line 122. The vertical signal line 122 is connected to the pixels 111 of each column.

A plurality of column circuits 114 are disposed. The column circuit 114 is connected to the vertical signal line 122 of each column. The column circuit 114 performs signal processing on the pixel signal output from the pixel 111 to the vertical signal line 122. For example, the signal processing performed by the column circuit 114 is noise reduction, signal amplification, AD conversion, and the like. Therefore, the column circuit 114 is an AD conversion circuit that converts the pixel signal read from the plurality of pixels 11 into a digital pixel signal.

The horizontal scanning circuit 113 sequentially transfers a plurality of pixel signals read from the pixels 111 of plurality of columns to the data generation circuit 102. The horizontal scanning circuit 113 outputs a control signal to the plurality of column circuits 114. The horizontal scanning circuit 113 causes the plurality of column circuits 114 to sequentially output the digital pixel signal to a horizontal signal line 123. The horizontal signal line 123 is connected to the plurality of column circuits 114 and the data generation circuit 102. The digital pixel signal sequentially output from the plurality of column circuits 114 to the horizontal signal line 123 is transferred to the data generation circuit 102 by the horizontal signal line 123.

The data generation circuit 102 includes an output circuit 115. The output circuit 115 embeds the first clock signal into the digital pixel signal at a timing that is based on the timing signal output from the timing generation circuit 116. In this way, the output circuit 115 generates the first digital data. The output circuit 115 converts the form of the first digital data into a form suitable for fast signal transmission. The output circuit 115 is connected to a signal output terminal 125. The signal output terminal 125 is connected to the transmitter 103. The first digital data generated by the output circuit 115 is output to the signal output terminal 125. The first digital data is output to the transmitter 103 via the signal output terminal 125.

Figure 3:
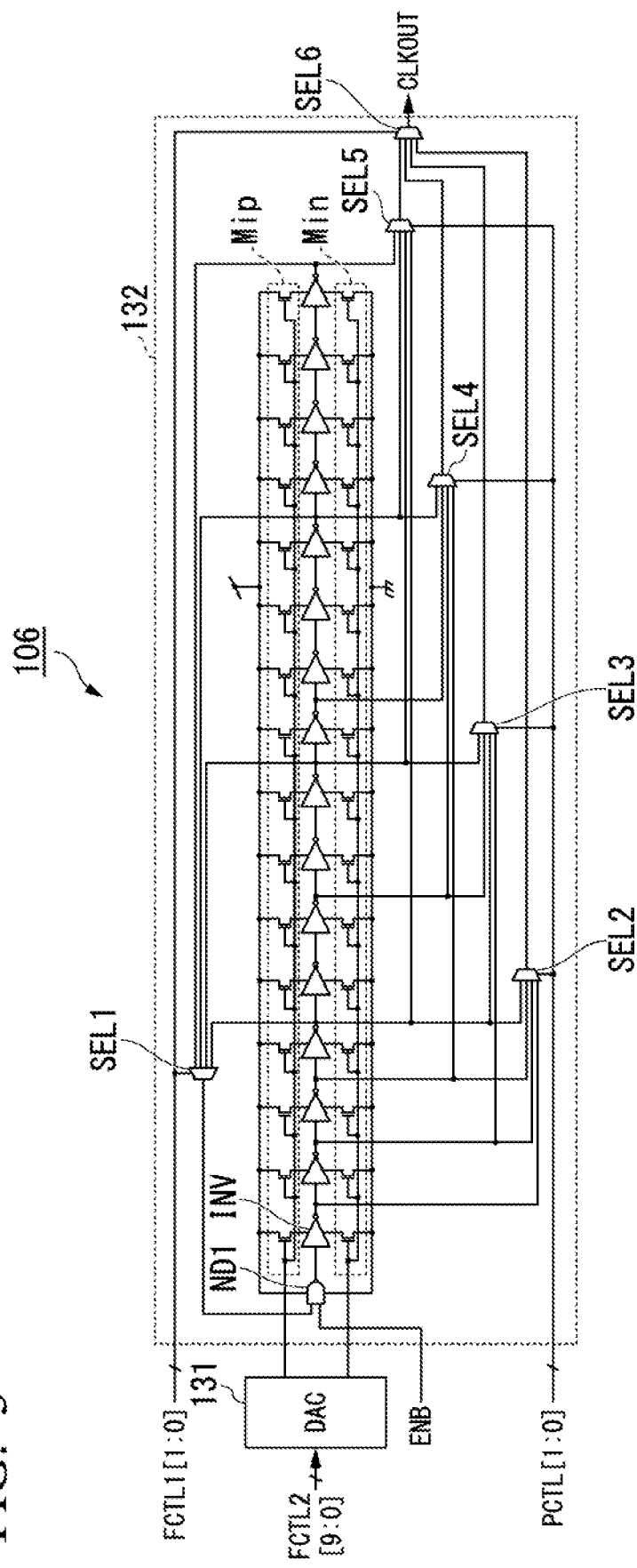
FIG. 3 is a circuit diagram showing a configuration of a clock generation circuit according to the first embodiment of the present invention.

FIG. 3 shows a configuration of the clock generation circuit 106. The clock generation circuit 106 shown in FIG. 3 includes a DAC 131 and a ring oscillator 132.

The DAC 131 is a digital-analog converter and converts the third digital data into an analog voltage. The ring oscillator 132 is a voltage-controlled oscillator (VCO) and generates a first clock signal CLKOUT on the basis of the analog voltage generated by the DAC 131.

The third digital data held in the memory 105 includes frequency adjustment data FCTL. For example, the frequency adjustment data FCTL are data of 12 bits. The frequency adjustment data FCTL includes first frequency adjustment data FCTL and second frequency adjustment data FCTL2. For example, the first frequency adjustment data FCTL1 are data of 2 bits and constitute the upper bits of the frequency adjustment data FCTL. For example, the second frequency adjustment data FCTL2 are data of 10 bits and constitute the lower bits of the frequency adjustment data FCTL. The first frequency adjustment data FCTL1 are output from the memory 105 to the ring oscillator 132. The second frequency adjustment data FCTL2 are output from the memory 105 to the DAC 131. The DAC 131 generates a first voltage and a second voltage on the basis of the second frequency adjustment data FCTL2. The first voltage and the second voltage generated by the DAC 131 are output to the ring oscillator 132.

The ring oscillator 132 consists of a ring oscillator circuit including at least four inverters INV (delay circuit). A reference numeral of one inverter INV is shown as a representative in FIG. 3. In the example shown in FIG. 3, sixteen inverters INV are disposed. The number of inverters INV is not limited to sixteen. The ring oscillator 132 further includes a NAND circuit ND1, a plurality of transistors Mip, a plurality of transistors Min, a selector SEL1, a selector SEL2, a selector SEL3, a selector SEL4, a selector SEL5, and a selector SEL6.

The NAND circuit ND1 and a plurality of inverters RO are connected in series to each other. The inverter INV connected to an output terminal of the NAND circuit ND1 is defined as a first inverter. The inverter INV connected to an output terminal of an N-th inverter is defined as an (N+)-th inverter. The numeral N is a natural number of any one of one to fifteen. An enable signal ENB and an output signal of the sixteenth inverter are input to the NAND circuit ND1. The enable signal ENB is output from the timing generation circuit 116. When the state of the enable signal ENB changes, a pulse signal starts to be transmitted in the NAND circuit ND1 and the plurality of inverters INV.

Each of the plurality of transistors Mip is connected to a first power source terminal of any one of the plurality of inverters INV. Each of the plurality of transistors Min is connected to a second power source terminal of any one of the plurality of inverters INV. The first voltage and the second voltage are output from the DAC 131. The first voltage is applied to the plurality of transistors Mip and the second voltage is applied to the plurality of transistors Min. The current that is based on the first voltage and the second voltage is supplied to the plurality of inverters INV by the plurality of transistors Mip and the plurality of transistors Min. The delay time of the plurality of inverters INV changes on the basis of the first voltage and the second voltage.

A delay time t in each of the plurality of inverters INV is represented by following Expression (1).

$$t = V\text{th} * C\text{in} / I\text{supply} \quad (1)$$

In Expression (1), a voltage Vth is a threshold value of each inverter INV. In Expression (1), a capacitance Cin is an input capacitance of each inverter IN. In Expression (1), a current amount Isupply is the amount of current supplied to each inverter INV. The current amount Isupply changes on the basis of the first voltage and the second voltage. The pulse signal has a cycle that is based on the delay time in one inverter NV the number of inverters INV, and the delay time in the NAND circuit ND. The frequency of the pulse signal changes on the basis of the first voltage and the second voltage.

The selector SEL1 is connected to an output terminal of each of the fourth inverter, the eighth inverter, the twelfth inverter, and the sixteenth inverter. The pulse signal output from each of the fourth inverter, the eighth inverter, the twelfth inverter, and the sixteenth inverter is input to the selector SEL1. The first frequency adjustment data FCTL1 are input to the selector SEL1. The selector SEL1 selects anyone of a plurality of pulse signals on the basis of the first frequency adjustment data FCTL1. The selector SEL1 outputs the selected pulse signal to the NAND circuit ND1.

The first frequency adjustment data FCTL1 represent the number of inverters INV included in the ring oscillator circuit. In a case in which the selector SEL1 outputs the pulse signal output from the fourth inverter, the NAND circuit ND1 and four inverters INV are included in the ring oscillator circuit. In a case in which the selector SEL1 outputs the pulse signal output from the eighth inverter, the NAND circuit ND1 and eight inverters INV are included in the ring oscillator circuit. In a case in which the selector SEL1 outputs the pulse signal output from the twelfth inverter, the NAND circuit ND1 and twelve inverters INV are included in the ring oscillator circuit. In a case in which the selector SEL1 outputs the pulse signal output from the sixteenth inverter, the NAND circuit ND1 and sixteen inverters INV are included in the ring oscillator circuit.

The number of inverters INV included in the ring oscillator circuit is represented as $4n$. The numeral n is a natural number of any one of one to four. The first clock signal has a frequency that is based on the number of inverters INV that are annularly connected together. When the numeral n is changed from one to two, the number of inverters INV is changed from four to eight. For this reason, the frequency of the pulse passing through the NAND circuit ND1 and the plurality of inverters INV becomes almost half.

The selector SEL2 is connected to an output terminal of each of the first inverter, the second inverter, the third inverter, and the fourth inverter. The pulse signal output from each of the first inverter, the second inverter, the third inverter, and the fourth inverter is input to the selector SEL2. The phases of a plurality of pulse signals input to the selector SEL2 are different from each other.

The selector SEL3 is connected to an output terminal of each of the second inverter, the fourth inverter, the sixth inverter, and the eighth inverter. The pulse signal output from each of the second inverter, the fourth inverter, the sixth inverter, and the eighth inverter is input to the selector SEL3. The phases of a plurality of pulse signals input to the selector SEL3 are different from each other.

The selector SEL4 is connected to an output terminal of each of the third inverter, the sixth inverter, the ninth inverter, and the twelfth inverter. The pulse signal output from each of the third inverter, the sixth inverter, the ninth inverter, and the twelfth inverter is input to the selector SEL4. The phases of a plurality of pulse signals input to the selector SEL4 are different from each other.

The selector SEL5 is connected to an output terminal of each of the fourth inverter, the eighth inverter, the twelfth inverter, and the sixteenth inverter. The pulse signal output from each of the fourth inverter, the eighth inverter, the twelfth inverter, and the sixteenth inverter is input to the selector SEL5. The phases of a plurality of pulse signals input to the selector SEL5 are different from each other.

The second digital data held in the memory 105 includes phase adjustment data PCTL. For example, the phase adjustment data PCTL are data of two bits. The phase adjustment data PCTL are output from the memory 105 to the ring oscillator 132. The phase adjustment data PCTL are input to the selector SEL2, the selector SEL3, the selector SEL4, and the selector SEL5. Each of the selector SEL2, the selector SEL3, the selector SEL4, and the selector SEL5 selects any one of the plurality of pulse signals on the basis of the phase adjustment data PCTL. Each of the selector SEL2, the selector SEL3, the selector SEL4, and the selector SEL5 outputs the selected pulse signal.

The selector SEL6 is connected to an output terminal of each of the selector SEL2, the selector SEL3, the selector SEL4, and the selector SEL5. The pulse signal output from each of the selector SEL2, the selector SEL3, the selector SEL4, and the selector SEL5 is input to the selector SEL6. The first frequency adjustment data FCTL is input to the selector SEL6. The selector SEL6 selects any one of the plurality of pulse signals on the basis of the first frequency adjustment data FCTL1. The selector SEL6 outputs the selected pulse signal as the first clock signal CLKOUT.

In a case in which the selector SEL1 outputs the pulse signal output from the fourth inverter, the selector SEL6 outputs the pulse signal output from the selector SEL2. In a case in which the selector SEL1 outputs the pulse signal output from the eighth inverter, the selector SEL6 outputs the pulse signal output from the selector SEL3. In a case in which the selector SEL1 outputs the pulse signal output from the twelfth inverter, the selector SEL6 outputs the pulse signal output from the selector SEL4. In a case in which the selector SEL1 outputs the pulse signal output from the sixteenth inverter, the selector SEL6 outputs the pulse signal output from the selector SEL5.

The frequency comparator 210 generates the third digital data that include the first frequency adjustment data FCTL1 as the upper bits and include the second frequency adjustment data FCTL2 as the lower bits. The frequency comparator 210 may generate the third digital data that include the first frequency adjustment data FCTL1 as the lower bits and include the second frequency adjustment data FCTL2 as the upper bits. The clock generation circuit 106 adjusts the number of inverters INV that are annularly connected together on the basis of the first frequency adjustment data FCTL1 and adjusts the amount of current supplied to the inverter INV on the basis of the second frequency adjustment data FCTL2. In this way, the clock generation circuit 106 adjusts the frequency of the first clock signal. The frequency comparator 210 can greatly change the frequency of the first clock signal by changing the number of inverters INV that are annularly connected together. The frequency comparator 210 can finely change the frequency of the first clock signal by changing the amount of current supplied to the inverter INV.

When the pulse is transferred in the ring oscillator 132, the NAND circuit ND1 and at least two inverters INV are annularly connected together. As long as the NAND circuit ND1 and an even number of inverters INV are annularly connected together, the number of inverters INV that are annularly connected together is not limited to the above-described example.

Figure 4:
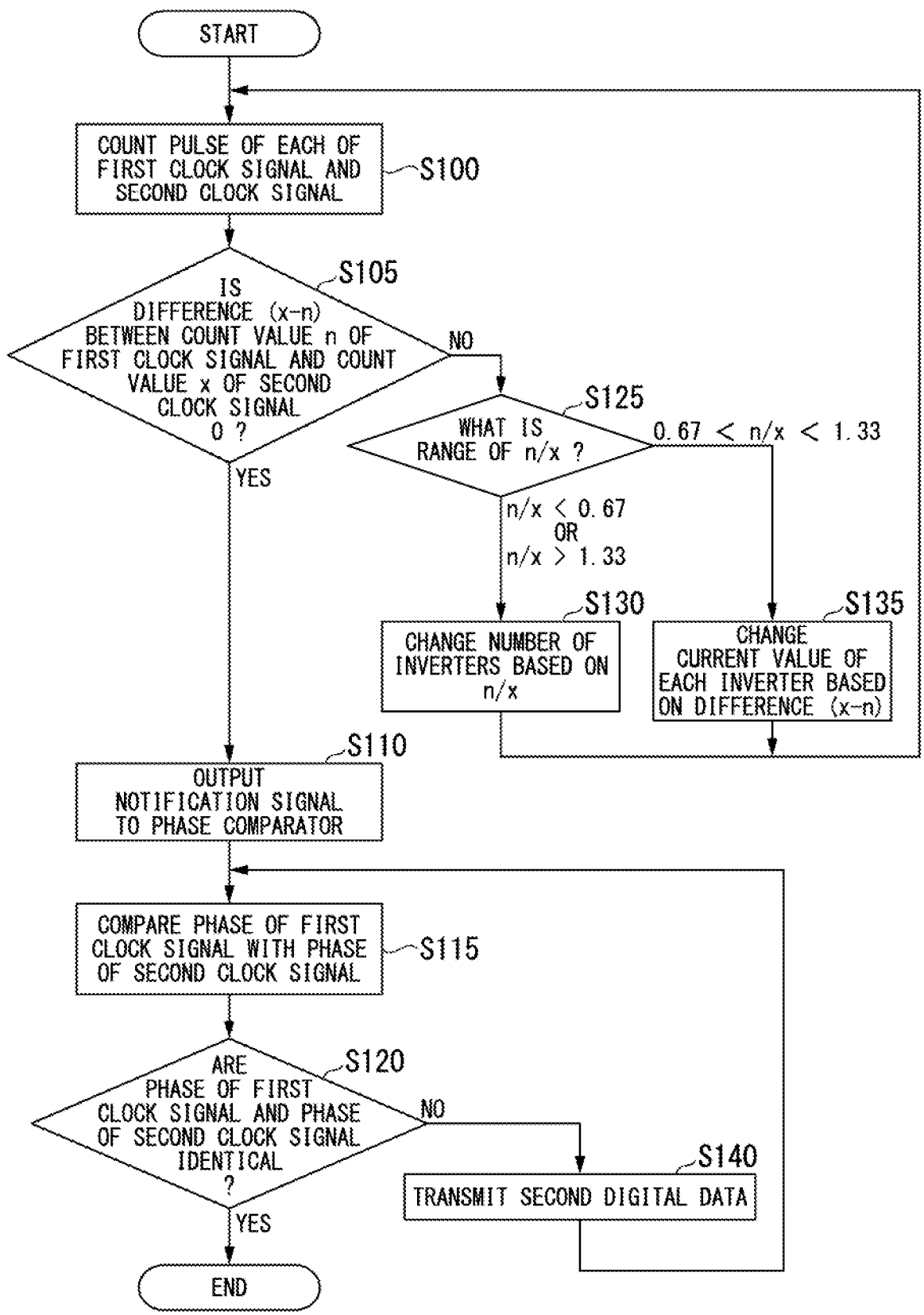
FIG. 4 is a flow chart showing an operation of the electronic endoscope system according to the first embodiment of the present invention.

FIG. 4 shows an operation for adjusting the frequency and the phase of the first clock signal. In the example shown in FIG. 3, four, eight, twelve, or sixteen inverters INV are annularly connected together. An operation of the electronic endoscope system ES1 will be described in a case in which twelve inverters INV are annularly connected together.

The frequency comparator 210 counts a pulse of each of the first clock signal and the second clock signal. For example, when the count value of the second clock signal becomes a predetermined number x, the frequency comparator 210 stops counting (Step S100).

After Step S100, the frequency comparator 210 determines whether or not the difference (x-n) between a count value n of the first clock signal and a count value x of the second clock signal is 0 (Step S105).

When the frequency comparator 210 determines that the difference (x-n) is 0 in Step S105, the frequency comparator 210 outputs the notification signal to the phase comparator 206 (Step S110). After Step S110, the phase comparator 206 compares the phase of the first clock signal with the phase of the second clock signal (Step S115).

After Step S115, the phase comparator 206 determines whether or not the phase of the first clock signal and the phase of the second clock signal are the same (Step S120).

When the phase comparator 206 determines that the phase of the first clock signal and the phase of the second clock signal are the same in Step S120, the processing shown in FIG. 4 is completed. When the phase comparator 206 determines that the phase of the first clock signal and the phase of the second clock signal are not the same in Step S120, the phase comparator 206 generates the second digital data that represent the difference between the phase of the first clock signal and the phase of the second clock signal. The phase comparator 206 outputs the second digital data to the transmitter 207. The transmitter 207 transmits the second digital data to the scope 1 (Step S140). After Step S140, Step S115 is executed.

When the frequency comparator 210 determines that the difference (x-n) is not 0 in Step S105, the frequency comparator 210 calculates a ratio (n/x) between the count value n of the first clock signal and the count value x of the second clock signal. The frequency comparator 210 determines the range of the ratio (n/x)(Step S125).

In order to simplify the description, the delay time of the NAND circuit ND1 is neglected. In a case in which sixteen inverters INV instead of twelve inverters INV are annularly connected together, the number of inverters INV becomes 16/12 times, that is, 1.33 times. For this reason, the frequency of the first clock signal becomes 12/16 times, that is, 0.75 times. In a case in which eight inverters INV instead of twelve inverters INV are annularly connected together, the number of inverters INV becomes 8/12 times, that is, 0.67 times. For this reason, the frequency of the first clock signal becomes 12/8 times, that is, 1.5 times.

In a case in which the ratio (n/x) is less than 0.67, the frequency of the first clock signal needs to be increased. In this case, eight or four inverters INV instead of twelve inverters INV need to be annularly connected together. In a case in which the ratio (n/x) is greater than 1.33, the frequency of the first clock signal needs to be decreased. In this case, sixteen inverters INV instead of twelve inverters INV need to be annularly connected together. When the ratio (n/x) is less than 0.67 or greater than 1.33, the frequency comparator 210 generates the third digital data including the first frequency adjustment data FCTL1 on the basis of the ratio (n/x). The frequency comparator 210 outputs the third digital data to the transmitter 207. The transmitter 207 transmits the third digital data to the scope 1 (Step S130). After Step S130, Step S100 is executed.

In a case in which the ratio (n/x) is greater than 0.67 and less than 1.33, the frequency of the first clock signal needs to be finely changed. The frequency comparator 210 generates the third digital data including the second frequency adjustment data FCTL2 on the basis of the difference (x-n). The frequency comparator 210 outputs the third digital data to the transmitter 207. The transmitter 207 transmits the third digital data to the scope 1 (Step S135). After Step S135, Step S100 is executed. The second frequency adjustment data FCTL2 are data for changing the amount of current supplied to each inverter INV. When the amount of current changes, the delay time in the inverter INV changes in accordance with above-described Expression (1). For this reason, the frequency of the first clock signal changes.

The frequency comparator 210 shown in FIG. 1 is not essential. The clock generation circuit 106 may generate the first clock signal on the basis of only the second digital data generated by the phase comparator 206.

In the first embodiment, the scope 1 does not include a quartz crystal oscillator. For this reason, the electronic endoscope system ES1 can miniaturize the scope 1. The first clock signal is generated on the basis of the second digital data and the third digital data transmitted from the processor 2. For this reason, the electronic endoscope system ES1 can supply a clock signal having a stable frequency to the imaging device 10. In the electronic endoscope system ES1, omission of frames is suppressed and a quality image is transmitted to the processor 2.

A clock signal is not transmitted from the processor 2 to the scope 1. The second digital data and the third digital data for controlling generation of a clock signal are transmitted from the processor 2 to the scope 1. Compared to a case in which a high-speed clock signal is transmitted, the degree of influence due to the noise is small.

The clock generation circuit 106 controls the frequency of the first clock signal on the basis of the second digital data and the third digital data. For this reason, fluctuation of the frequency due to factors such as temperature and a power source voltage is suppressed. Since the clock generation circuit 106 includes a digital-analog converter and a voltage-controlled oscillator, the configuration of the clock generation circuit 106 is simplified.

The transmitter 207 does not need to always transmit the second digital data and the third digital data. The transmitter 207 may intermittently transmit the second digital data and the third digital data. Even in a period in which the second digital data and the third digital data are not transmitted, the second digital data and the third digital data are output from the memory 105 to the clock generation circuit 106. For this reason, the clock generation circuit 106 can stably generate a clock signal.

The clock generation circuit 106 adjusts the frequency of the first clock signal on the basis of the third digital data generated by the frequency comparator 210. Thereafter, the clock generation circuit 106 adjusts the phase of the first clock signal on the basis of the second digital data generated by the phase comparator 206. In a case in which the frequency of the first clock signal greatly changes due to the influence of temperature, noise, and the like, the clock generation circuit 106 can promptly adjust the frequency. In addition, it is possible to prevent the phase of the first clock signal from being adjusted in a state in which the frequency of the first clock signal and the frequency of the second clock signal are shifted from each other.

The clock generation circuit 106 can greatly change the frequency of the first clock signal on the basis of the first frequency adjustment data FCTL1. The clock generation circuit 106 can finely change the frequency of the first clock signal on the basis of the second frequency adjustment data FCTL2.

Second Embodiment

Figure 5:
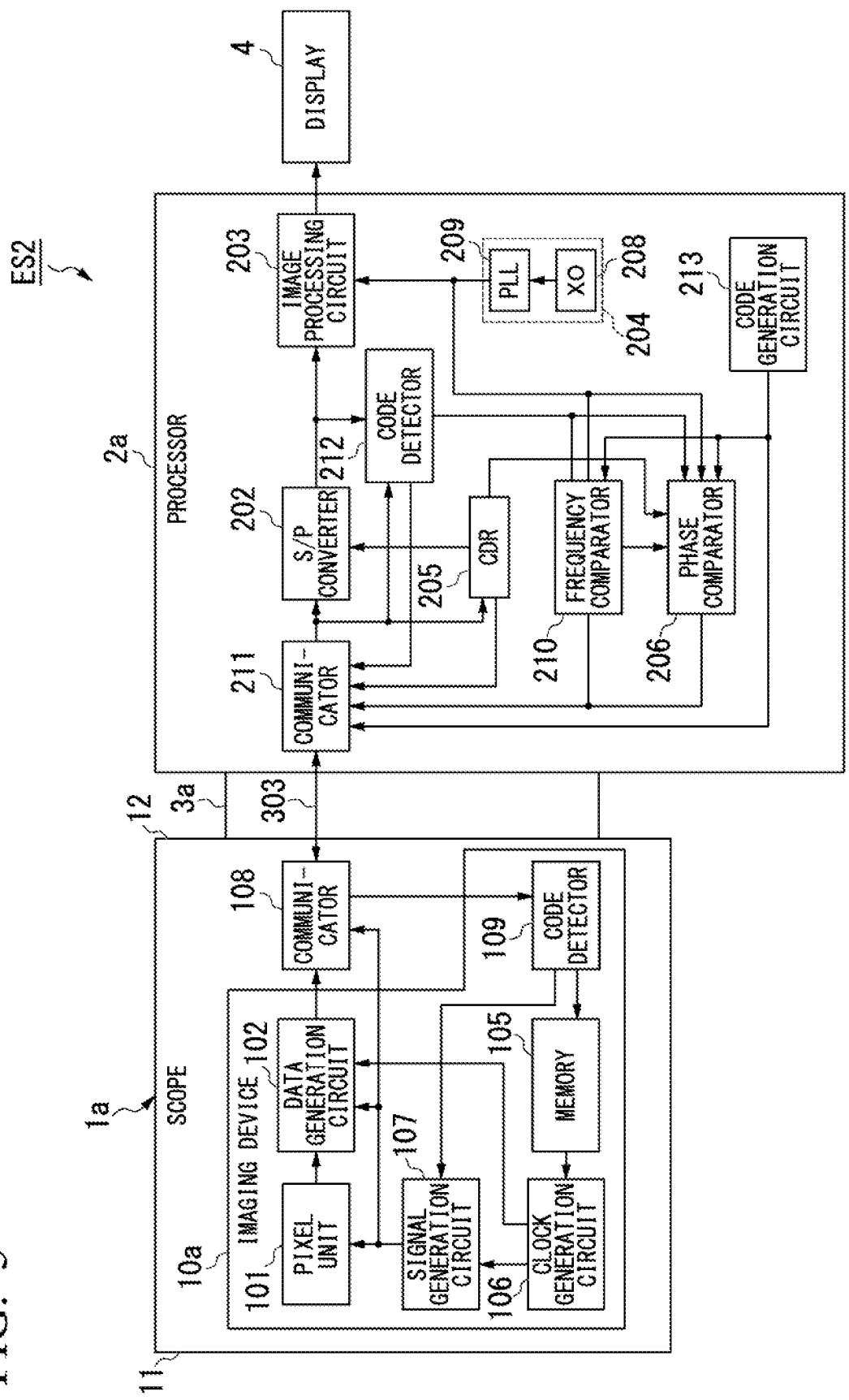
FIG. 5 is a block diagram showing a configuration of an electronic endoscope system according to a second embodiment of the present invention.

FIG. 5 shows a configuration of an electronic endoscope system ES2 according to a second embodiment of the present invention. The same part as the part shown in FIG. 1 will not be described.

The scope 1 shown in FIG. 1 is changed to a scope 1a. The scope 1a includes an imaging device 10a and a communicator 108. The imaging device 10 shown in FIG. 1 is changed to the imaging device 10a. The imaging device 10a includes a pixel unit 101, a data generation circuit 102, a memory 105, a clock generation circuit 106, a signal generation circuit 107, and a code detector 109.

The processor 2 shown in FIG. 1 is changed to a processor 2a. The processor 2a includes an S/P converter 202, an image processing circuit 203, a clock generation circuit 204, a CDR circuit 205, a phase comparator 206, a frequency comparator 210, a communicator 211, a code detector 212, and a code generation circuit 213. In the processor 2a, the receiver 201 shown in FIG. 1 is changed to the communicator 211. The processor 2a does not include the transmitter 207 shown in FIG. 1.

The communicator 108 (first communicator) transmits first digital data to the processor 2a in a period excluding a blanking period. The communicator 211 (second communicator) receives the first digital data transmitted from the scope 1a. The communicator 211 transmits second digital data to the scope 1a in the blanking period. The communicator 108 receives the second digital data transmitted from the processor 2a in the blanking period.

The imaging device 10a completes generation of image data in the blanking period. In the blanking period, the output of effective image data from the imaging device 10a is stopped. The blanking period intermittently occurs. In a period between two blanking periods, the imaging device 10a generates image data that are based on a pixel signal read from a pixel 111 of one row.

The communicator 211 transmits third digital data to the scope 1a in the blanking period. The communicator 108 receives the third digital data transmitted from the processor 2a in the blanking period. For example, the second digital data and the third digital data are transmitted in respective blanking periods different from each other. For example, the communicator 211 transmits the third digital data to the scope 1a in a first blanking period. The communicator 211 transmits the second digital data to the scope 1a in a second blanking period after the first blanking period.

For example, between the first blanking period and the second blanking period, a pixel signal is read from the pixel 111 of at least one row and data of at least one row included in the image data are output from the imaging device 10a. In a case in which a pixel signal is read from the pixel 111 of at least two rows between the first blanking period and the second blanking period, a blanking period is inserted each time a pixel signal is read from the pixel 111 of one row.

The data generation circuit 102 generates an end code that represents a timing at which generation of the image data is intermittently stopped. The end code represents a timing at which generation of data of one row included in the image data is completed and a blanking period is started. When generation of the image data is intermittently stopped, the communicator 108 transmits the end code to the processor 2a. The communicator 211 receives the end code transmitted from the scope 1a. When the end code is received, the communicator 211 starts transmission of the second digital data or the third digital data.

The code generation circuit 213 generates a start code that represents a timing at which generation of the image data is started. The start code represents a timing at which the blanking period is completed. The communicator 211 transmits the start code to the scope 1a in the blanking period. The communicator 108 receives the start code transmitted from the processor 2a in the blanking period. When the start code is received, the signal generation circuit 107 generates a control signal for causing the imaging device 10a to start generation of the image data. When the start code is received, the data generation circuit 102 starts generation of the first digital data. When the start code is received, the communicator 108 starts transmission of the first digital data.

While the communicator 108 transmits the first digital data, the communicator 211 does not transmit the second digital data or the third digital data. While the communicator 211 transmits the second digital data or the third digital data, the communicator 108 does not transmit the first digital data.

When the imaging device 10a completes generation of data of one row included in the image data, the communicator 108 transmits the end code to the processor 2a. The communicator 211 receives the end code transmitted from the scope 1a. The frequency comparator 210 generates a count value by counting a pulse of the second clock signal in a counting period. The counting period is included in a horizontal reading period from the timing at which the start code is transmitted to the timing at which the end code is received. The frequency comparator 210 generates the third digital data on the basis of a result of comparing the count value with an estimation value calculated in advance. The estimation value is a count value that is assumed to be obtained by counting a pulse of the second clock signal in the counting period when it is assumed that the frequency of the first clock signal and the frequency of the second clock signal are the same.

The cable 3 shown in FIG. 1 is changed to a cable 3a. The cable 3a includes a signal line 303. The communicator 108 and the communicator 211 are connected to the signal line 303. The first digital data transmitted from the communicator 108 and the end code transmitted from the communicator 108 pass through the signal line 303. The second digital data and the third digital data transmitted from the communicator 211 and the start code transmitted from the communicator 211 pass through the signal line 303.

The communicator 108 and the communicator 211 may perform wireless communication. For example, the communicator 108 and the communicator 211 include an antenna and a wireless circuit.

The data generation circuit 102 outputs the end code to the communicator 108 after outputting the first digital data to the communicator 108. The communicator 108 transmits the end code to the processor 2a after transmitting the first digital data to the processor 2a.

The communicator 211 receives the end code transmitted by the communicator 108 after receiving the first digital data transmitted by the communicator 108. A data sequence including the first digital data and the end code is output to the code detector 212. The code detector 212 detects the end code from the data sequence received by the communicator 211. When the end code is detected, the code detector 212 outputs a transmission start signal to the communicator 211. The communicator 211 starts transmission of the second digital data or the third digital data on the basis of the transmission start signal.

The code generation circuit 213 generates the start code at a predetermined timing. For example, the predetermined timing is a timing at which a predetermined time passes from a timing at which the end code is detected. The predetermined timing may be determined by the processor 2a at its discretion. The start code generated by the code generation circuit 213 is output to the phase comparator 206, the frequency comparator 210, and the communicator 211. The communicator 211 transmits the start code to the scope 1a after transmitting the second digital data or the third digital data to the scope 1a.

When the start code is output from the code generation circuit 213, the frequency comparator 210 starts counting of a pulse of the second clock signal. While the communicator 211 receives the first digital data, the frequency comparator 210 counts a pulse of the second clock signal. When the end code is detected, the code detector 212 outputs the end code to the frequency comparator 210. When the end code is output from the code detector 212, the frequency comparator 210 stops counting of a pulse of the second clock signal.

The number of data of one row included in the image data is set in advance. For example, the data of one row include data generated on the basis of a pixel signal read from the pixel 111 of the M-th column. The numeral M is a natural number of two or more. For example, a start timing of the counting period is the same as a start timing of the horizontal reading period and an end timing of the counting period is the same as an end timing of the horizontal reading period.

It is possible to calculate the length of a period necessary for transmitting M pieces of data in advance when it is assumed that the imaging device 10a is driven by using the first clock signal having the same frequency as the frequency of the second clock signal. A count value is calculated as the estimation value in advance when it is assumed that the frequency comparator 210 counts a pulse of the second clock signal in the period. For example, the processor 2a includes a circuit that calculates the above-described estimation value. For example, the processor 2a includes a memory that stores the calculated estimation value. The frequency comparator 210 reads the estimation value from the memory and compares the count value of the second clock signal with the estimation value. The frequency comparator 210 calculates the difference between the count value of the second clock signal and the estimation value and generates the third digital data on the basis of the difference. The frequency comparator 210 outputs the third digital data to the communicator 211.

The start timing of the counting period may not be the same as the start timing of the horizontal reading period. The counting period may be started after the start timing of the horizontal reading period. The end timing of the counting period may not be the same as the end timing of the horizontal reading period. The counting period may be completed before the end timing of the horizontal reading period.

When the frequency of the first clock signal and the frequency of the second clock signal match each other, the frequency comparator 210 outputs a notification signal to the phase comparator 206. The notification signal represents that the first clock signal having the same frequency as the frequency of the second clock signal has been generated. For example, in the horizontal reading period of data of the N-th row included in the image data, the notification signal is output to the phase comparator 206. After the notification signal is output from the frequency comparator 210, the start code is output from the code generation circuit 213 and the horizontal reading period of data of the (N+1)-th row included in the image data is started. At this time, the phase comparator 206 compares the phase of the first clock signal with the phase of the second clock signal and generates second digital data. The phase comparator 206 outputs the second digital data to the communicator 211.

The communicator 108 receives the start code transmitted by the communicator 211 after receiving the second digital data or the third digital data transmitted by the communicator 211. A data sequence including one of the second digital data and the third digital data and the start code is output to the code detector 109. The code detector 109 detects the start code from the data sequence received by the communicator 108. The code detector 109 outputs the second digital data or the third digital data excluding the start code to the memory 105. The memory 105 holds the second digital data or the third digital data output from the code detector 109.

When the start code is detected, the code detector 109 outputs a code detection signal to the signal generation circuit 107. The signal generation circuit 107 generates a control signal for starting generation and transmission of the image data on the basis of the code detection signal. The control signal generated by the signal generation circuit 107 is output to the pixel unit 101, the data generation circuit 102, and the communicator 108. The pixel unit 101 starts generation of the pixel signal on the basis of the control signal. The data generation circuit 102 starts generation of the first digital data on the basis of the control signal. The communicator 108 starts transmission of the first digital data on the basis of the control signal.

The end code may be embedded into the image data. The CDR circuit 205 may detect the end code by reproducing the end code from the first digital data.

Figure 6:
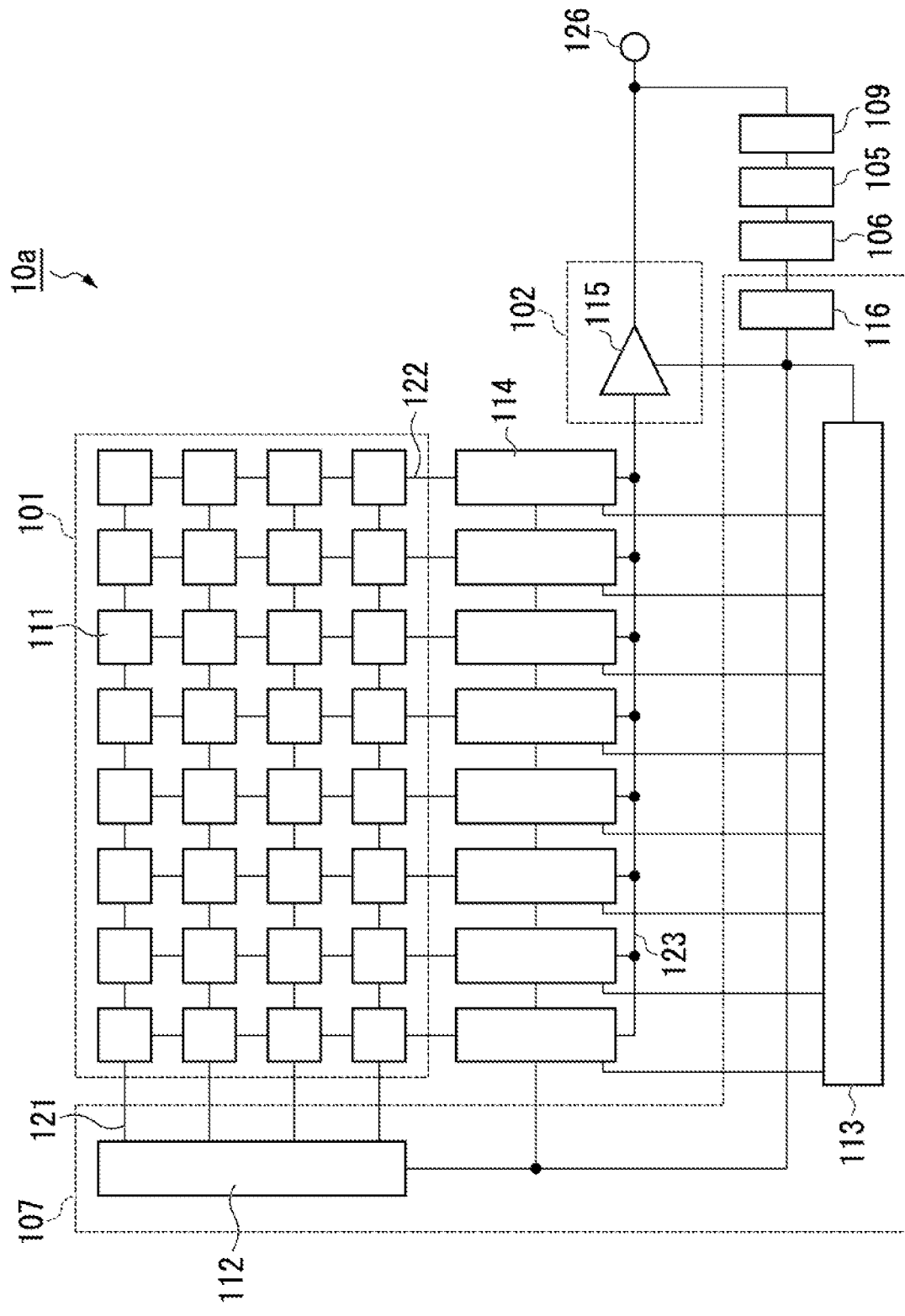
FIG. 6 is a block diagram showing a configuration of an imaging device according to the second embodiment of the present invention.

FIG. 6 shows a configuration of the imaging device 10. The same part as the part shown in FIG. 2 will not be described.

In the imaging device 10a, a signal input/output terminal 126 is disposed instead of the signal input terminal 124 and the signal output terminal 125. The code detector 109 and the output circuit 115 are connected to the signal input/output terminal 126. The signal input/output terminal 126 is connected to the communicator 108. The second digital data or the third digital data received by the communicator 108 and the start code received by the communicator 108 are input to the code detector 109 via the signal input/output terminal 126. The output circuit 115 generates the first digital data and the end code. The first digital data generated by the output circuit 115 and the end code generated by the output circuit 115 are output to the signal input/output terminal 126. The first digital data and the end code are output to the communicator 108 via the signal input/output terminal 126.

Figure 7:
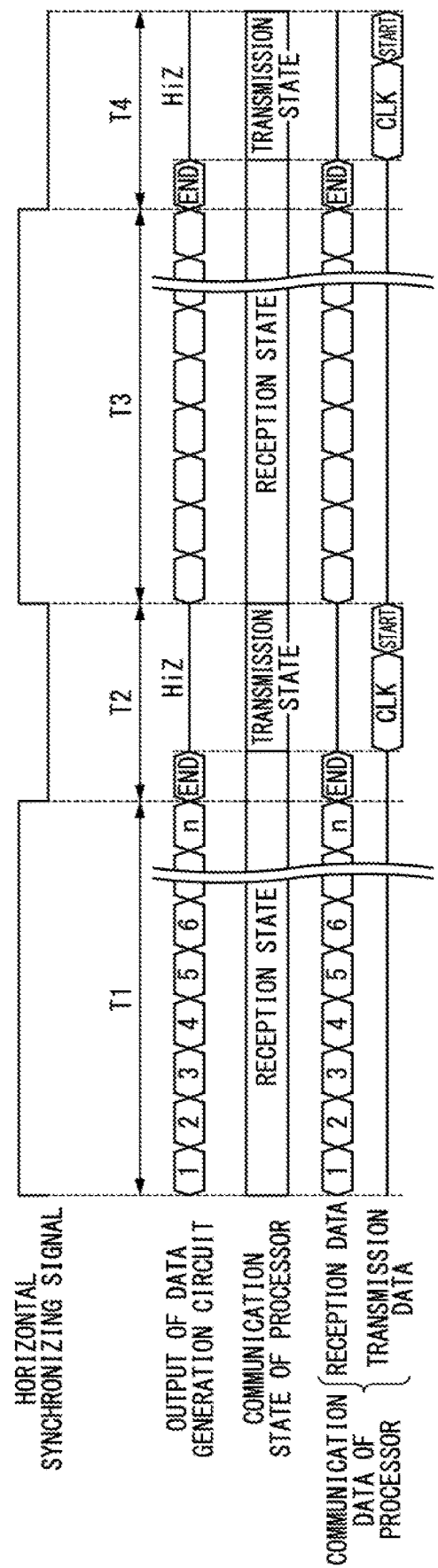
FIG. 7 is a timing chart showing an operation of the electronic endoscope system according to the second embodiment of the present invention.

FIG. 7 shows an operation of the electronic endoscope system ES2. In FIG. 7, a waveform of a horizontal synchronizing signal generated by the timing generation circuit 116 is shown. In FIG. 7, a data sequence of the first digital data and an end code END output from the data generation circuit 102 is shown. In FIG. 7, a communication state of the processor 2a and communication data of the processor 2a are shown. The communication data of the processor 2a include reception data received by the communicator 211 and transmission data transmitted by the communicator 211. The reception data include the first digital data and the end code END, the transmission data include clock control data CLK and a start code START, the clock control data CLK are the second digital data or the third digital data. In FIG. 7, time passes in the right direction.

When the electronic endoscope system ES2 is activated, for example, the clock generation circuit 106 generates the first clock signal on the basis of a predetermined voltage. The predetermined voltage is the voltage designed for the first clock signal to be synchronized with the second clock signal.

The pixel unit 101 outputs a pixel signal in a horizontal reading period T1. The data generation circuit 102 generates the first digital data in the horizontal reading period T1. The data to which a number is attached in FIG. 7 are image data that are based on a pixel signal of each column in a predetermined row. The communicator 108 transmits the first digital data in the horizontal reading period T1. The length of the horizontal reading period T1 is controlled on the basis of the timing signal, that is, the horizontal synchronizing signal generated by the signal generation circuit 107.

The processor 2a is in the reception state in the horizontal reading period T1. The communicator 211 receives the first digital data. The CDR circuit 205 reproduces the first clock signal from the first digital data. The frequency comparator 210 starts counting of a pulse of the second clock signal. The frequency comparator 210 counts a pulse of the second clock signal in the horizontal reading period T1.

When the horizontal reading period T1 is completed, a blanking period T2 is started. When the horizontal reading period T1 is completed, the pixel unit 101 completes the output of the pixel signal. When the horizontal reading period T1 is completed, the data generation circuit 102 generates the end code. The communicator 108 transmits the end code to the processor 2a. After the end code is generated, the data generation circuit 102 is in a high impedance state.

The communicator 211 receives the end code. When the end code is received, the code detector 212 outputs the transmission start signal to the communicator 211 and outputs the end code to the frequency comparator 210. The frequency comparator 210 stops counting of a pulse of the second clock signal. The frequency comparator 210 calculates the difference between the count value of the second clock signal and the estimation value and generates the third digital data on the basis of the difference. The frequency comparator 210 outputs the third digital data to the communicator 211.

The communicator 211 starts transmission of the third digital data (clock control data CLK) on the basis of the transmission start signal. After the end code is received, the communication state of the processor 2a is a transmission state. The communicator 211 transmits the third digital data in the blanking period T2.

The communicator 108 receives the third digital data in the blanking period T2. The code detector 109 outputs the third digital data to the memory 105. The memory 105 holds the third digital data. The clock generation circuit 106 generates the first clock signal on the basis of the third digital data held in the memory 105.

The code generation circuit 213 generates the start code at a predetermined timing. When the start code is generated, the communicator 211 completes transmission of the third digital data and transmits the start code to the scope 1a.

The communicator 108 receives the start code. The code detector 109 detects the start code. When the start code is detected, a horizontal reading period T3 is started. When the start code is detected, the signal generation circuit 107 generates a control signal for starting generation and transmission of the image data. The pixel unit 101 starts generation of the pixel signal on the basis of the control signal. The data generation circuit 102 starts generation of the first digital data on the basis of the control signal. The communicator 108 starts transmission of the first digital data on the basis of the control signal.

When the start code is output from the code generation circuit 213, the frequency comparator 210 starts counting of a pulse of the second clock signal. An operation in the horizontal reading period T3 is similar to the operation in the horizontal reading period T1. When the horizontal reading period T3 is completed, a blanking period T4 is started. An operation in the blanking period T4 is similar to the operation in the blanking period T2.

The electronic endoscope system ES2 executes an operation similar to the operation in each of the horizontal reading period T1 and the blanking period T2 until the frequency of the first clock signal and the frequency of the second clock signal match each other. In FIG. 7, an operation executed before the horizontal reading period T1 is started is not shown. Before the horizontal reading period T1 is started, an operation similar to the operation in each of the horizontal reading period T1 and the blanking period T2 is repeated.

An operation in a case in which the count value of the second clock signal obtained in the horizontal reading period T1 matches the estimation value will be described. The frequency comparator 210 outputs the notification signal to the phase comparator 206 in the blanking period T2. The frequency comparator 210 generates the third digital data and outputs the third digital data to the communicator 211. The communicator 211 transmits the third digital data to the scope 1a in the blanking period T2. Since the frequency of the first clock signal and the frequency of the second clock signal are the same, generation and transmission of the third digital data may be omitted.

When the notification signal is output from the frequency comparator 210, the phase comparator 206 waits in order to start comparison of phases. When the start code is output from the code generation circuit 213, the phase comparator 206 starts comparing the phase of the first clock signal with the phase of the second clock signal. The phase comparator 206 generates the second digital data that represent the difference between the phase of the first clock signal and the phase of the second clock signal.

The communicator 211 receives the end code. When the end code is received, the code detector 212 outputs the transmission start signal to the communicator 211 and outputs the end code to the phase comparator 206. The phase comparator 206 outputs the second digital data to the communicator 211.

The communicator 211 starts transmission of the second digital data (clock control data CLK) on the basis of the transmission start signal. The communicator 211 transmits the second digital data to the scope 1a in the blanking period T4.

The communicator 108 receives the second digital data in the blanking period T4. The code detector 109 outputs the second digital data to the memory 105. The memory 105 holds the second digital data. The clock generation circuit 106 generates the first clock signal on the basis of the second digital data held in the memory 105.

While the frequency comparator 210 counts a pulse of the second clock signal, the phase comparator 206 may stop its operation. While the phase comparator 206 compares the phase of the first clock signal with the phase of the second clock signal, the frequency comparator 210 may stop its operation.

The frequency comparator 210 and the phase comparator 206 may simultaneously operate. For example, the frequency comparator 210 starts counting of a pulse of the second clock signal and, at the same time, the phase comparator 206 starts comparing the phase of the first clock signal with the phase of the second clock signal. The phase comparator 206 keeps the output of the second digital data to the communicator 211 stopped until the notification signal is output from the frequency comparator 210.

When the count value matches the estimation value, the frequency comparator 210 outputs the notification signal to the phase comparator 206 and stops the output of the third digital data to the communicator 211. When the notification signal is output from the frequency comparator 210 and the end code is output from the code detector 212, the phase comparator 206 outputs the second digital data to the communicator 211. The communicator 211 transmits the second digital data to the scope 1a in the blanking period. For example, when the count value of the second clock signal obtained in the horizontal reading period T1 is the same as the estimation value, the communicator 211 transmits the second digital data to the scope 1a in the blanking period T2.

In the above-described example, when the start code is output from the code generation circuit 213, the frequency comparator 210 starts counting of a pulse of the second clock signal. Given the delay or the like in the cable 3a, there is a possibility that a timing at which the start code is generated and a timing at which reception of the first digital data is started are not the same. The communicator 108 may transmit the start code to the processor 2a before transmitting the first digital data to the processor 2a. The communicator 211 receives the start code transmitted by the communicator 108. A data sequence including the start code is output to the code detector 212. The code detector 212 detects the start code from the data sequence received by the communicator 211. When the start code is detected by the code detector 212, the frequency comparator 210 may start counting of a pulse of the second clock signal.

The frequency comparator 210 shown in FIG. 5 is not essential. The clock generation circuit 106 may generate the first clock signal on the basis of only the second digital data generated by the phase comparator 206.

The frequency comparator 210 may count a pulse of the first clock signal reproduced by the CDR circuit 205. The frequency comparator 210 may calculate the difference between the count value of the first clock signal and the count value of the second clock signal and generate the third digital data.

In the second embodiment, the communicator 108 and the communicator 211 perform communication in a first direction in the horizontal reading period. The communicator 108 and the communicator 211 perform communication in a second direction in the blanking period. In case of wired communication, the number of signal lines connecting the scope 1a and the processor 2a together is reduced. For this reason, the cable 3 becomes thin and the scope 1a is miniaturized. In case of wireless communication, the number of communicators is reduced and the scope 1a is miniaturized.

When generation of the image data is completed, the end code is transmitted from the scope 1*a* to the processor 2*a*. The processor 2*a* can become aware of the start timing of the blanking period on the basis of the end code.

The start code is transmitted from the processor 2*a* to the scope 1*a* at a timing at which the blanking period is completed. The length of the blanking period is decided on the basis of the timing at which the start code is transmitted. The electronic endoscope system ES2 can set a frame rate by adjusting the timing at which the start code is transmitted.

Since the frequency comparator 210 does not need to count a pulse of the first clock signal, the number of circuits using a high frequency signal is reduced. Consequently, the power consumption and the circuit scale are reduced.

Third Embodiment

Figure 8:
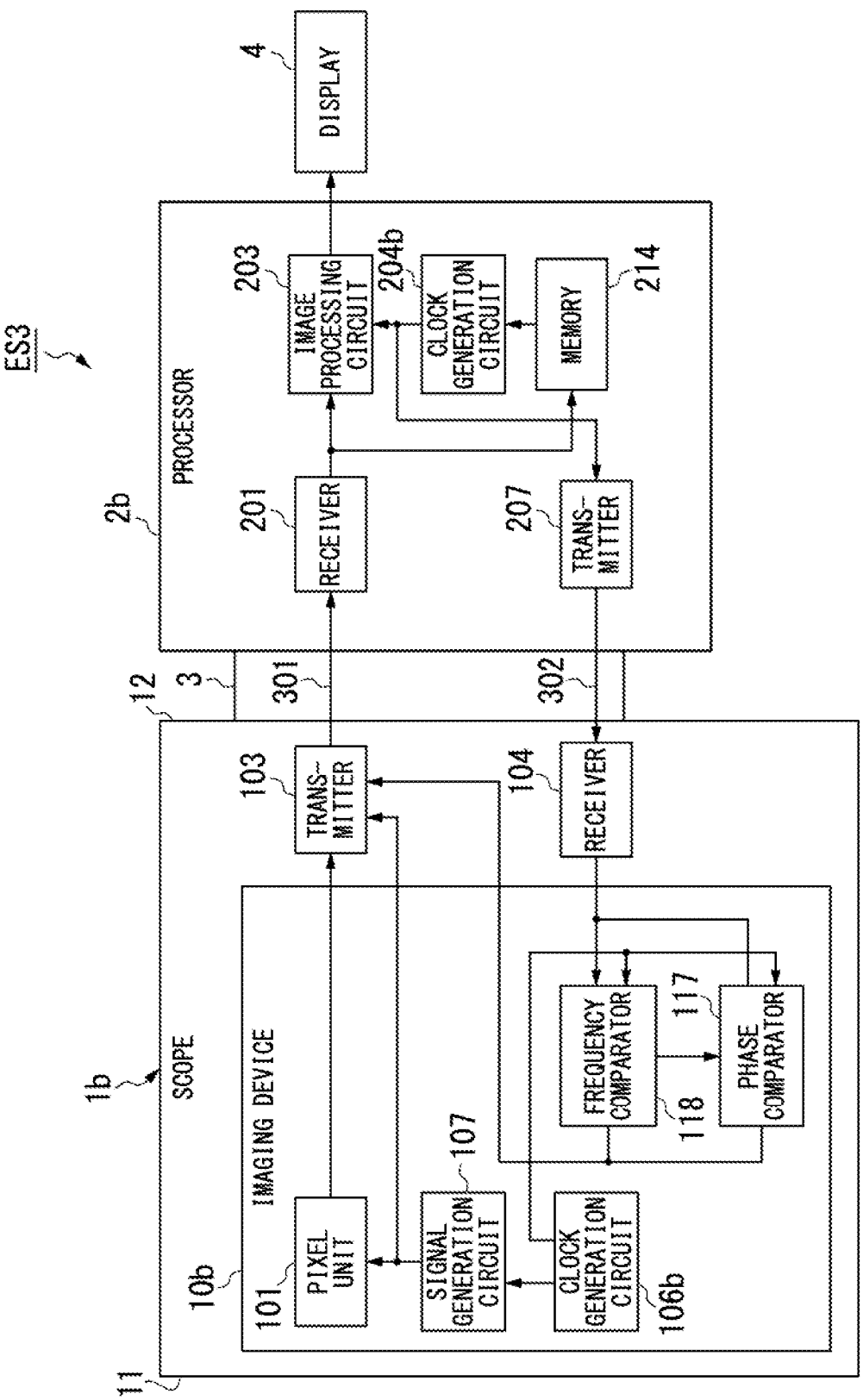
FIG. 8 is a block diagram showing a configuration of an electronic endoscope system according to a third embodiment of the present invention.

FIG. 8 shows a configuration of an electronic endoscope system ES3 according to a third embodiment of the present invention. The same part as the part shown in FIG. 1 will not be described.

The scope 1 shown in FIG. 1 is changed to a scope 1*b*. The scope 1*b* includes an imaging device 10*b*, a transmitter 103, and a receiver 104. The imaging device 10 shown in FIG. 1 is changed to the imaging device 10*b*. The imaging device 10*b* includes a pixel unit 101, a clock generation circuit 106*b*, a signal generation circuit 107, a phase comparator 117, and a frequency comparator 118. In the imaging device 10*b*, the clock generation circuit 106 shown in FIG. 1 is changed to the clock generation circuit 106*b*. The imaging device 10*b* does not include the data generation circuit 102 and the memory 105 shown in FIG. 1.

The processor 2 shown in FIG. 1 is changed to a processor 2*b*. The processor 2*b* includes a receiver 201, an image processing circuit 203, a clock generation circuit 204*b*, a transmitter 207, and a memory 214. In the processor 2*b*, the clock generation circuit 204 shown in FIG. 1 is changed to the clock generation circuit 204*b*. The processor 2*b* does not include the S/P converter 202, the CDR circuit 205, the phase comparator 206, and the frequency comparator 210 shown in FIG. 1.

The transmitter 103 (first communicator) transmits image data to the processor 2*b* in a period excluding a blanking period. The phase comparator 117 compares the phase of a first clock signal with the phase of a second clock signal and generates digital phase data that represent the difference between the phase of the first clock signal and the phase of the second clock signal. The receiver 201 (second communicator) receives the image data transmitted from the scope 1*b*. The clock generation circuit 204*b* generates the second clock signal.

The transmitter 207 (second communicator) transmits the second clock signal to the scope 1*b* in the blanking period. The receiver 104 (first communicator) receives the second clock signal transmitted from the processor 2*b* in the blanking period. The transmitter 103 transmits the digital phase data to the processor 2*b* in the blanking period. The receiver 201 receives the digital phase data transmitted from the scope 1*b* in the blanking period. The clock generation circuit 204*b* generates the second clock signal synchronized with the first clock signal on the basis of the digital phase data.

The frequency comparator 118 compares the frequency of the first clock signal with the frequency of the second clock signal and generates digital frequency data that represent the difference between the frequency of the first clock signal and the frequency of the second clock signal. The transmitter 103 transmits the digital frequency data to the processor 2*b* in the blanking period. The receiver 201 receives the digital frequency data transmitted from the scope 1*b* in the blanking period. The clock generation circuit 204*b* generates the second clock signal having the same frequency as the frequency of the first clock signal by adjusting the frequency of the second clock signal on the basis of the digital frequency data.

The memory 214 holds the digital phase data and the digital frequency data received by the receiver 201. The memory 214 outputs the digital phase data and the digital frequency data to the clock generation circuit 204*b*.

The clock generation circuit 106*b* includes a configuration similar to the configuration of the clock generation circuit 204 shown in FIG. 1. For example, the clock generation circuit 106*b* includes a crystal oscillator and a PLL circuit. The clock generation circuit 204*b* includes a configuration similar to the configuration of the clock generation circuit 106 shown in FIG. 1. For example, the clock generation circuit 204*b* includes a DAC and a ring oscillator.

For example, after the frequency comparator 118 detects that the frequency of the first clock signal and the frequency of the second clock signal match each other, the phase comparator 117 compares the phase of the first clock signal with the phase of the second clock signal and generates the digital phase data. The clock generation circuit 204*b* adjusts the phase of the second clock signal on the basis of the digital phase data after adjusting the frequency of the second clock signal on the basis of the digital frequency data.

The second clock signal is generated on the basis of the digital phase data and the digital frequency data transmitted from the scope 1*b*. For this reason, the electronic endoscope system ES3 can generate the second clock signal synchronized with the first clock signal.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly the invention is not to be considered as being limited by the foregoing description, and is only limited by the scope of the appended claims.

What is claimed is:

1. An imaging system comprising:
   a camera unit; and
   a main body,
   wherein the camera unit includes:
      a solid-state imaging device configured to generate image data on the basis of a control signal;
      a first clock generation circuit configured to generate a first clock signal;
      a signal generation circuit configured to generate the control signal on the basis of the first clock signal;
      a data generation circuit configured to generate first digital data by embedding the first clock signal into the image data; and
      a first communicator configured to perform communication in a first direction in which the first digital data are transmitted to the main body in a period different from a blanking period,
   the main body includes:
      a second communicator configured to receive the first digital data transmitted from the camera unit;
      a clock detection circuit configured to detect the first clock signal from the first digital data;
      a second clock generation circuit configured to generate a second clock signal; and a phase comparator configured to compare a phase of the first clock signal with a phase of the second clock signal and generate second digital data that represent a difference between the phase of the first clock signal and the phase of the second clock signal, the second communicator is configured to perform communication in a second direction in which the second digital data are transmitted to the camera unit in the blanking period, the first communicator is configured to receive the second digital data transmitted from the main body in the blanking period, the camera unit and the main body are connected by only one signal line through which the first digital data pass in the communication in the first direction and the second digital data pass in the communication in the second direction, and the first clock generation circuit is configured to generate the first clock signal synchronized with the second clock signal on the basis of the second digital data, wherein the data generation circuit is configured to generate an end code that represents a timing at which generation of the image data is intermittently stopped, the first communicator is configured to transmit the end code to the main body when the generation of the image data is intermittently stopped, the second communicator is configured to receive the end code transmitted from the camera unit, and the second communicator is configured to start transmission of the second digital data when the end code is received.

2. The imaging system according to claim 1,
wherein the main body further includes a code generation circuit configured to generate a start code that represents a timing at which the generation of the image data is started, the second communicator is configured to transmit the start code to the camera unit in the blanking period, the first communicator is configured to receive the start code transmitted from the main body in the blanking period, the signal generation circuit is configured to generate the control signal for causing the solid-state imaging device to start the generation of the image data when the start code is received, the data generation circuit is configured to start generation of the first digital data when the start code is received, and the first communicator is configured to start transmission of the first digital data when the start code is received.

3. The imaging system according to claim 1,
wherein the camera unit further includes a memory configured to hold the second digital data, and the first clock generation circuit is configured to generate the first clock signal on the basis of the second digital data held in the memory.

4. An imaging system comprising:
a camera unit; and
a main body,
wherein the camera unit includes:
a solid-state imaging device configured to generate image data on the basis of a control signal;
a first clock generation circuit configured to generate a first clock signal;
a signal generation circuit configured to generate the control signal on the basis of the first clock signal;

a data generation circuit configured to generate first digital data by embedding the first clock signal into the image data; and a first communicator configured to perform communication in a first direction in which the first digital data are transmitted to the main body in a period different from a blanking period, the main body includes:
a second communicator configured to receive the first digital data transmitted from the camera unit;
a clock detection circuit configured to detect the first clock signal from the first digital data;
a second clock generation circuit configured to generate a second clock signal; and
a phase comparator configured to compare a phase of the first clock signal with a phase of the second clock signal and generate second digital data that represent a difference between the phase of the first clock signal and the phase of the second clock signal, the second communicator is configured to perform communication in a second direction in which the second digital data are transmitted to the camera unit in the blanking period, the first communicator is configured to receive the second digital data transmitted from the main body in the blanking period, the camera unit and the main body are connected by only one signal line through which the first digital data pass in the communication in the first direction and the second digital data pass in the communication in the second direction, the first clock generation circuit is configured to generate the first clock signal synchronized with the second clock signal on the basis of the second digital data, wherein the main body further includes a frequency comparator configured to compare a frequency of the first clock signal with a frequency of the second clock signal and generate third digital data that represent a difference between the frequency of the first clock signal and the frequency of the second clock signal, the second communicator is configured to transmit the third digital data to the camera unit in the blanking period, the first communicator is configured to receive the third digital data transmitted from the main body in the blanking period, the first clock generation circuit is configured to generate the first clock signal having the same frequency as the frequency of the second clock signal by adjusting the frequency of the first clock signal on the basis of the third digital data, wherein the second communicator is configured to transmit the third digital data to the camera unit until the frequency comparator detects that the frequency of the first clock signal and the frequency of the second clock signal are the same, and the second communicator is configured to transmit the second digital data to the camera unit after the frequency comparator detects that the frequency of the first clock signal and the frequency of the second clock signal are the same.

5. An imaging system comprising:
a camera unit; and
a main body,
wherein the camera unit includes:
a solid-state imaging device configured to generate image data on the basis of a control signal;

a first clock generation circuit configured to generate a first clock signal;

a signal generation circuit configured to generate the control signal on the basis of the first clock signal;

a data generation circuit configured to generate first digital data by embedding the first clock signal into the image data; and a first communicator configured to perform communication in a first direction in which the first digital data are transmitted to the main body in a period different from a blanking period, the main body includes:

a second communicator configured to receive the first digital data transmitted from the camera unit;

a clock detection circuit configured to detect the first clock signal from the first digital data;

a second clock generation circuit configured to generate a second clock signal; and a phase comparator configured to compare a phase of the first clock signal with a phase of the second clock signal and generate second digital data that represent a difference between the phase of the first clock signal and the phase of the second clock signal, the second communicator is configured to perform communication in a second direction in which the second digital data are transmitted to the camera unit in the blanking period, the first communicator is configured to receive the second digital data transmitted from the main body in the blanking period, the camera unit and the main body are connected by only one signal line through which the first digital data pass in the communication in the first direction and the second digital data pass in the communication in the second direction, the first clock generation circuit is configured to generate the first clock signal synchronized with the second clock signal on the basis of the second digital data, wherein the main body further includes a frequency comparator configured to compare a frequency of the first clock signal with a frequency of the second clock signal and generate third digital data that represent a difference between the frequency of the first clock signal and the frequency of the second clock signal, the second communicator is configured to transmit the third digital data to the camera unit in the blanking period, the first communicator is configured to receive the third digital data transmitted from the main body in the blanking period, the first clock generation circuit is configured to generate the first clock signal having the same frequency as the frequency of the second clock signal by adjusting the frequency of the first clock signal on the basis of the third digital data, wherein the blanking period includes a first blanking period and a second blanking period after the first blanking period, the second communicator is configured to transmit the third digital data to the camera unit in the first blanking period, and the second communicator is configured to transmit the second digital data to the camera unit in the second blanking period.

6. The imaging system according to claim 4, wherein the second communicator is configured to transmit a start code that represents a timing at which the generation of the image data is started to the camera unit in the blanking period, the first communicator is configured to receive the start code transmitted from the main body in the blanking period, the signal generation circuit is configured to generate the control signal for causing the solid-state imaging device to start the generation of the image data when the start code is received, the data generation circuit is configured to start generation of the first digital data when the start code is received, the first communicator is configured to start transmission of the first digital data when the start code is received, the first communicator is configured to transmit an end code that represents a timing at which generation of data of one row included in the image data is completed to the main body when the solid-state imaging device completes the generation of the data of the one row, the second communicator is configured to receive the end code transmitted from the camera unit, the frequency comparator is configured to generate a count value by counting a pulse of the second clock signal in a counting period included in a horizontal reading period from a timing at which the start code is transmitted to a timing at which the end code is received, and the frequency comparator is configured to generate the third digital data on the basis of a result of comparing the count value with an estimation value calculated in advance, the estimation value being a count value that is assumed to be obtained by counting the pulse of the second clock signal in the counting period when it is assumed that the frequency of the first clock signal and the frequency of the second clock signal are the same.

7. The imaging system according to claim 4, wherein the first clock generation circuit includes a ring oscillator circuit including at least four delay circuits, the frequency comparator is configured to generate the third digital data including first frequency adjustment data and second frequency adjustment data, and the first clock generation circuit is configured to adjust the frequency of the first clock signal by adjusting a number of the delay circuits that are annularly connected together on the basis of the first frequency adjustment data and by adjusting an amount of current supplied to the delay circuits on the basis of the second frequency adjustment data.

8. The imaging system according to claim 4, wherein the frequency comparator is configured to generate the third digital data that include the first frequency adjustment data as an upper bit and include the second frequency adjustment data as a lower bit.

9. The imaging system according to claim 4, wherein the signal generation circuit includes:

a digital-analog converter configured to convert the third digital data into an analog voltage; and a voltage-controlled oscillator configured to generate the first clock signal on the basis of the analog voltage.

10. An endoscope system comprising:

a scope including a tip end and a base end; and an imaging system according to claim 1, wherein the solid-state imaging device is disposed in the tip end, and the main body is connected to the base end.

11. The imaging system according to claim 5, wherein the second communicator is configured to transmit a start code that represents a timing at which the generation of the image data is started to the camera unit in the blanking period, the first communicator is configured to receive the start code transmitted from the main body in the blanking period, the signal generation circuit is configured to generate the control signal for causing the solid-state imaging device to start the generation of the image data when the start code is received, the data generation circuit is configured to start generation of the first digital data when the start code is received, the first communicator is configured to start transmission of the first digital data when the start code is received, the first communicator is configured to transmit an end code that represents a timing at which generation of data of one row included in the image data is completed to the main body when the solid-state imaging device completes the generation of the data of the one row, the second communicator is configured to receive the end code transmitted from the camera unit, the frequency comparator is configured to generate a count value by counting a pulse of the second clock signal in a counting period included in a horizontal reading period from a timing at which the start code is transmitted to a timing at which the end code is received, and the frequency comparator is configured to generate the third digital data on the basis of a result of comparing the count value with an estimation value calculated in advance, the estimation value being a count value that is assumed to be obtained by counting the pulse of the second clock signal in the counting period when it is assumed that the frequency of the first clock signal and the frequency of the second clock signal are the same.

12. The imaging system according to claim 5, wherein the first clock generation circuit includes a ring oscillator circuit including at least four delay circuits, the frequency comparator is configured to generate the third digital data including first frequency adjustment data and second frequency adjustment data, and the first clock generation circuit is configured to adjust the frequency of the first clock signal by adjusting a number of the delay circuits that are annularly connected together on the basis of the first frequency adjustment data and by adjusting an amount of current supplied to the delay circuits on the basis of the second frequency adjustment data.

13. The imaging system according to claim 5, wherein the frequency comparator is configured to generate the third digital data that include the first frequency adjustment data as an upper bit and include the second frequency adjustment data as a lower bit.

14. The imaging system according to claim 5, wherein the signal generation circuit includes:

a digital-analog converter configured to convert the third digital data into an analog voltage; and a voltage-controlled oscillator configured to generate the first clock signal on the basis of the analog voltage.

* * * * *